United States Patent
Gröbke Zbinden et al.

(10) Patent No.: US 7,678,917 B2
(45) Date of Patent: Mar. 16, 2010

(54) FACTOR XA INHIBITORS

(75) Inventors: Katrin Gröbke Zbinden, Liestal (CH); Wolfgang Haap, Lörrach (DE); Hans Hilpert, Münchenstein (CH); Narendra Panday, Basel (CH); Fabienne Ricklin, Hombourg (FR)

(73) Assignee: Hoffman-La Roche Inc., Nutley, NJ (US)

( * ) Notice: Subject to any disclaimer, the term of this patent is extended or adjusted under 35 U.S.C. 154(b) by 666 days.

(21) Appl. No.: 11/510,831

(22) Filed: Aug. 25, 2006

(65) Prior Publication Data

US 2007/0049587 A1    Mar. 1, 2007

(30) Foreign Application Priority Data

Sep. 1, 2005  (EP) ................... 05107992

(51) Int. Cl.
C07D 409/00 (2006.01)
A61K 31/495 (2006.01)

(52) U.S. Cl. ........... 546/280.4; 514/231.5; 514/255.05; 514/336; 514/422; 544/146; 544/405; 548/527

(58) Field of Classification Search .............. 514/231.5, 514/255.05, 336, 422; 544/146, 405; 546/280.4; 548/527
See application file for complete search history.

(56) References Cited

U.S. PATENT DOCUMENTS 7,501,413 B2 *  3/2009  Boehringer et al. ...... 514/235.2

FOREIGN PATENT DOCUMENTS

| WO | WO 00/09463 | 2/2000 |
| WO | WO 03/045912 | 6/2003 |
| WO | WO 2004/082687 A1 | 9/2004 |
| WO | WO 2006/048152 A2 | 5/2006 |

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*

* cited by examiner

Primary Examiner—Shailendra Kumar
(74) Attorney, Agent, or Firm—George W. Johnston; Dennis P. Tramaloni; Brian C. Remy

(57) ABSTRACT

The invention is concerned with novel cycloalkane carboxamides of formula (I)

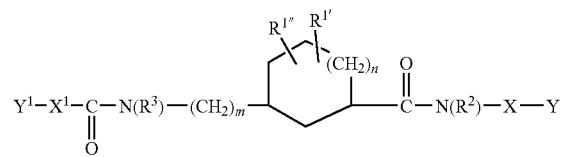

wherein $X$, $X^1$, $Y$, $Y^1$, $R^{1'}$, $R^{1''}$, $R^2$, $R^3$, m and n are as defined in the description and in the claims, as well as physiologically acceptable salts thereof. These compounds inhibit the coagulation factor Xa and can be used as medicaments.

21 Claims, No Drawings

FACTOR XA INHIBITORS

PRIORITY TO RELATED APPLICATIONS

This application claims the benefit of European Application No. 05107992.9, filed Sep. 1, 2005, which is hereby incorporated by reference in its entirety.

The invention is concerned with novel cycloalkane carboxamides of formula (I),

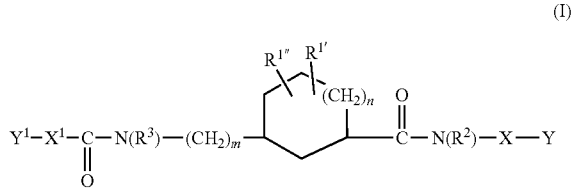

wherein $R^{1'}$ is selected from the group consisting of carboxyl, cyano, $C_{1-6}$ alkoxycarbonyl, hydroxy $C_{1-6}$ alkyl-NH—C(O)—, N($C_{1-6}$ alkyl)(hydroxy $C_{1-6}$ alkyl)-C(O)—, $C_{1-6}$ alkyl-NH—C(O)—, halo $C_{1-6}$ alkyl-NH—C(O)—, $C_{3-7}$ cycloalkyl-$C_{1-6}$ alkyl-NH—C(O)—, $C_{3-7}$ cycloalkyl-$C_{1-6}$ alkyl, $C_{3-7}$ cycloalkyl-$C_{1-6}$ alkoxy, hydroxy $C_{1-6}$ alkyl-, hydroxy, $C_{1-6}$ alkoxy, $C_{1-6}$ alkoxy-$C_{1-6}$ alkyl-, halo $C_{1-6}$ alkoxy-$C_{1-6}$ alkyl-, halo $C_{1-6}$ alkyl, halo $C_{1-6}$ alkoxy, heterocyclyl-$C_{1-6}$ alkyl-, $C_{1-6}$ alkyl-sulfonylamino-$C_{1-6}$ alkyl-, ($C_{1-6}$ alkyl-sulfonyl)($C_{1-6}$ alkyl)amino-$C_{1-6}$ alkyl-, $C_{1-6}$ alkyl-carbonylamino-$C_{1-6}$ alkyl-, hydroxy-$C_{2-6}$ alkoxy-, amino, mono- or di-$C_{1-6}$ alkyl substituted amino, mono- or di-$C_{1-6}$ alkyl substituted amino-$C_{1-6}$ alkyl-, mono- or di-halo $C_{1-6}$ alkyl substituted amino, $C_{3-7}$ cycloalkylamino-$C_{1-6}$ alkyl-, heterocyclyl-amino-$C_{1-6}$ alkyl-, ($C_{3-7}$ cycloalkyl)($C_{1-6}$ alkyl)amino-$C_{1-6}$ alkyl-, (heterocyclyl)($C_{1-6}$ alkyl) amino-$C_{1-6}$ alkyl-, $C_{1-6}$ alkyl-sulfonylamino-, $C_{1-6}$ alkyl-carbonylamino-, ($C_{1-6}$ alkylcarbonyl)($C_{1-6}$ alkyl) amino-, ($C_{1-6}$ alkoxy-carbonyl)($C_{1-6}$ alkyl)amino-, ($C_{1-6}$ alkylsulfonyl)($C_{1-6}$ alkyl)amino-, optionally halogenated heterocyclyl, where one or two carbon atoms of the heterocyclyl are optionally replaced with a carbonyl group, halogen, ($C_{1-6}$ alkyl-carbonyl)($C_{1-6}$ alkyl)amino-$C_{1-6}$ alkyl-, $C_{1-6}$ alkyl-O—CO—NH—, $C_{1-6}$ alkyl-O—CO—NH—$C_{1-6}$ alkyl-, $C_{1-6}$ alkyl-NH—CO—NH—, $C_{1-6}$ alkyl-NH—CO—NH—$C_{1-6}$ alkyl-, aryl, heteroaryl, aryloxy, heteroaryloxy, aryl-$C_{1-6}$-alkoxy, heteroaryl-$C_{1-6}$-alkoxy, and NR'R"-$C_{1-6}$ alkyl- where R' and R", together with the nitrogen atom to which they are attached, form a lactam containing one to six carbon atoms;

$R^{1''}$ is hydrogen; or $R^{1'}$ and $R^{1''}$ form, together with the same carbon atom to which they are attached, a member selected from the group consisting of —C(=O)—, —C=CH$_2$, $C_{3-7}$ cycloalkyl, and heterocyclyl, where one or two carbon atoms of the heterocyclyl are optionally replaced with a carbonyl group;

$R^2$ is selected from the group consisting of hydrogen and $C_{1-6}$ alkyl;

$R^3$ is selected from the group consisting of hydrogen and $C_{1-6}$ alkyl;

X and $X^1$ are independently selected from the group consisting of arylene, heteroarylene and heterocyclylene, wherein the arylene, heteroarylene and heterocyclylene are optionally substituted by one or more substituents independently selected from the group consisting of $C_{1-6}$ alkyl, $C_{1-6}$ alkoxy, halogen, cyano, nitro, amino, —N(R')—CO—($C_{1-6}$ alkyl optionally substituted by one or more fluorine atoms), in which R' is selected from the group consisting of hydrogen, $C_{1-6}$ alkyl and fluoro $C_{1-6}$ alkyl, —N(R')—CO—O—($C_{1-6}$ alkyl optionally substituted by one or more fluorine atoms), in which R' is hydrogen, $C_{1-6}$ alkyl or fluoro $C_{1-6}$ alkyl, —N(R')—CO—N(R")(R'''), in which R', R" and R''' are independently hydrogen, $C_{1-6}$ alkyl or fluoro $C_{1-6}$ alkyl, —C(O)—N(R')(R"), in which R' and R" are independently hydrogen, $C_{1-6}$ alkyl or fluoro $C_{1-6}$ alkyl, or R' and R", together with the nitrogen atom to which they are attached, form heterocyclyl, —NR'R", in which R' and R" are independently hydrogen, $C_{1-6}$ alkyl or fluoro $C_{1-6}$ alkyl, or R' and R", together with the nitrogen atom to which they are attached, form heterocyclyl,

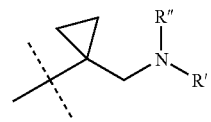

wherein R' and R" are independently $C_{1-6}$ alkyl or fluoro $C_{1-6}$ alkyl, or R' and R", together with the nitrogen atom to which they are attached, form heterocyclyl,

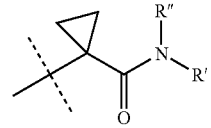

wherein R' and R" are independently $C_{1-6}$ alkyl or fluoro $C_{1-6}$ alkyl, or R' and R", together with the nitrogen atom to which they are attached, form heterocyclyl,

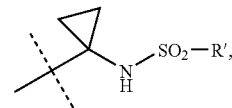

in which R' is fluoro $C_{1-6}$ alkyl and

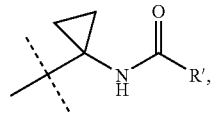

in which R' is fluoro $C_{1-6}$ alkyl,
where one or two carbon atoms of the heteroarylene and heterocyclylene are optionally replaced with a carbonyl group;

Y is selected from the group consisting of aryl, heteroaryl and heterocyclyl, where the aryl, heteroaryl and heterocyclyl are optionally substituted by one or more substituents independently selected from the group consisting of $C_{1-6}$ alkyl optionally substituted by one or more fluorine atoms, $C_{1-6}$ alkoxy optionally substituted by one or more fluorine atoms, halogen, cyano, nitro, amino, mono- or di-$C_{1-6}$ alkyl substituted amino, in which $C_{1-6}$ alkyl is optionally substituted by one or more fluorine atoms, mono- or di-$C_{1-6}$ alkyl substituted amino-$C_{1-6}$ alkyl, in which $C_{1-6}$ alkyl is optionally substituted by one or more fluorine atoms, —$SO_2$—$C_{1-6}$ alkyl, in which $C_{1-6}$ alkyl is optionally substituted by one or more fluorine atoms, —$SO_2$—$NH_2$, —$SO_2$—NH—$C_{1-6}$ alkyl, in which $C_{1-6}$ alkyl is optionally substituted by one or more fluorine atoms, and —$SO_2$—N($C_{1-6}$ alkyl)$_2$, in which $C_{1-6}$ alkyl is optionally substituted by one or more fluorine atoms, where one or two carbon atoms of the heteroaryl and heterocyclyl are optionally replaced with a carbonyl group;

$Y^1$ is selected from the group consisting of hydrogen, aryl, heteroaryl and heterocyclyl, where the aryl, heteroaryl and heterocyclyl are optionally substituted by one or more substituents independently selected from the group consisting of $C_{1-6}$ alkyl optionally substituted by one or more fluorine atoms, $C_{1-6}$ alkoxy optionally substituted by one or more fluorine atoms, halogen, cyano, nitro, amino, mono- or di-$C_{1-6}$ alkyl substituted amino, in which $C_{1-6}$ alkyl is optionally substituted by one or more fluorine atoms, mono- or di-$C_{1-6}$ alkyl substituted amino-$C_{1-6}$ alkyl, in which $C_{1-6}$ alkyl is optionally substituted by one or more fluorine atoms, —$SO_2$—$C_{1-6}$ alkyl, in which $C_{1-6}$ alkyl is optionally substituted by one or more fluorine atoms, —$SO_2$—$NH_2$, —$SO_2$—NH—$C_{1-6}$ alkyl, in which $C_{1-6}$ alkyl is optionally substituted by one or more fluorine atoms, and —$SO_2$—N($C_{1-6}$ alkyl)$_2$, in which $C_{1-6}$ alkyl is optionally substituted by one or more fluorine atoms, where one or two carbon atoms of the heteroaryl and heterocyclyl are optionally replaced with a carbonyl group;

m is 0 or 1;

n is 0 or 1;

and prodrugs and pharmaceutically acceptable salts thereof.

Further, the invention is concerned with a process and an intermediate for the manufacture of the above compounds, pharmaceutical preparations which contain such compounds, the use of these compounds for the production of pharmaceutical preparations as well as a process for the manufacture of the intermediate.

The compounds of formula (I) are active compounds and inhibit coagulation factor Xa.

These compounds consequently influence blood coagulation. They therefore inhibit the formation of thrombin and can be used for the treatment and/or prevention of thrombotic disorders, such as amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. They have potentially benefit in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumor agents.

Other inhibitors of factor Xa had previously been suggested for the inhibition of the formation of thrombin and for the treatment of related diseases. However, there is still a need for novel factor Xa inhibitors which exhibit improved pharmacological properties, e.g. an improved selectivity towards thrombin.

The present invention provides novel compounds of formula (I) which are factor Xa inhibitors. The compounds of the present invention unexpectedly inhibit coagulation factor Xa and also exhibit improved pharmacological properties compared to other compounds already known in the art.

Unless otherwise indicated, the following definitions are set forth to illustrate and define the meaning and scope of the various terms used to describe the invention herein.

The term "halogen" or "halo" means fluorine, chlorine, bromine and iodine, with fluorine, chlorine and bromine being preferred, and fluorine and chlorine being more preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. $C_{1-4}$ alkyl is more preferred.

The term "halo $C_{1-6}$ alkyl" means $C_{1-6}$ alkyl substituted by one or more same or different halogen atoms independently selected from the group consisting of chlorine, fluorine and bromine, such as $CF_3$.

The term "fluoro $C_{1-6}$ alkyl" means $C_{1-6}$ alkyl substituted by one or more, preferably one, two or three fluorine atoms.

The term "hydroxy $C_{1-6}$ alkyl" means $C_{1-6}$ alkyl substituted by one or more, preferably one hydroxy group.

The term "$C_{3-7}$ cycloalkyl", alone or in combination with other groups, means a saturated monovalent cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "aryl" means phenyl or naphthyl.

The term "arylene" means a divalent aryl group.

The term "phenylene", alone or in combination with other groups, means a divalent phenyl group. 1,4-phenylene is preferred.

The term "heterocyclyl", alone or combination with other groups, means non-aromatic mono- or bi-cyclic radicals of three to eight ring atoms in which one or two ring atoms are heteroatoms selected from N, O, or $S(O)_n$ (where n is an integer from 0 to 2), the remaining ring atoms being C.

The term "heterocyclylene", alone or combination with other groups, means a divalent heterocyclyl group as defined above.

The term "heteroaryl", alone or combination with other groups, means a monocyclic or bicyclic radical of 5 to 12 ring atoms having at least one aromatic ring containing one, two, or three ring heteroatoms selected from N, O, and S, the remaining ring atoms being C, with the understanding that the attachment point of the heteroaryl radical will be on an aromatic ring.

The term "heteroarylene", alone or combination with other groups, means a divalent heteroaryl group as defined above.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na-, K-, Ca- and trimethylammoniumsalt. The term "pharmaceutically acceptable salts" also refers to such salts. Acid addition salts as described above are preferred.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) Other preferred compounds of the invention are compounds of formula (I) wherein, $R^{1'}$ is selected from the group consisting of hydroxy, $C_{1-6}$ alkoxy and fluoro $C_{1-6}$ alkoxy;

$R^{1''}$ is hydrogen;

X is selected from the group consisting of phenylene, heteroarylene and heterocyclylene, where the phenylene, heteroarylene and heterocyclylene are optionally substituted by one or more substituents independently selected from the group consisting of $C_{1-6}$ alkyl, $C_{1-6}$ alkoxy and halogen;

Y is selected from the group consisting of phenyl, heteroaryl and heterocyclyl, where the phenyl, heteroaryl and heterocyclyl are optionally substituted by one or more substituents independently selected from the group consisting of $C_{1-6}$ alkyl, $C_{1-6}$ alkoxy, and halogen where one or two carbon atoms of the heteroaryl and heterocyclyl are optionally replaced with a carbonyl group;

$Y^1$—$X^1$— forms a member selected from the group consisting of phenylene, heteroarylene and heterocyclylene, where the phenylene, heteroarylene and heterocyclylene are optionally substituted by one or more substituents independently selected from the group consisting of $C_{1-6}$ alkyl, $C_{1-6}$ alkoxy and halogen; and n is 0.

ii) Other preferred compounds of the invention are compounds of formula (I), where X is 1,4-phenylene optionally substituted by one, two or three, preferably one, substituent selected from the group consisting of halogen and $C_{1-6}$ alkyl. 2-fluoro-1,4-phenylene is more preferred as X.

iii) Other preferred compounds of the invention are compounds of formula (I), where Y is selected from heteroaryl and heterocyclyl, where the heteroaryl and heterocyclyl are mono-cyclic radicals of six ring atoms in which one or two ring atoms are heteroatoms selected from N and O, the remaining ring atoms being C, where one carbon atom of the heteroaryl and heterocyclyl is replaced with a carbonyl group. Y is preferably pyridyl, pyrazinyl or morpholinyl, where one carbon atoms of the pyridyl, pyrazinyl and morpholinyl is replaced with a carbonyl group. 2-Oxo-1-pyridyl, 2-oxo-1-pyrazinyl or 3-oxo-4-morpholinyl is more preferred, and especially 2-oxo-1-pyridyl is preferred, as substituents at Y.

iv) Other preferred compounds of the invention are compounds of formula (I), where $Y^1$—$X^1$— forms heteroaryl optionally substituted by one or more halogen atoms. Heteroaryl formed by $Y^1$—$X^1$— is preferably mono-cyclic radical of five or six ring atoms in which one or two ring atoms are S, the remaining ring atoms being C, e.g., thienyl. 5-chloro-2-thienyl is especially preferred.

v) Other preferred compounds of the invention are compounds of formula (I), where $Y^1$ is hydrogen.

vi) Other preferred compounds of the invention are compounds of formula (I), where $R^2$ is hydrogen.

vii) Other preferred compounds of the invention are compounds of formula (I), where $R^3$ is hydrogen.

viii) Other preferred compounds of the invention are compounds of formula (I), where $R^{1'}$ is selected from the group consisting of hydroxy, $C_{1-6}$ alkoxy and fluoro $C_{1-6}$ alkoxy, preferably hydroxy, methoxy, ethoxy or 2,2-difluoroethoxy.

ix) Other preferred compounds of the invention are compounds of formula (Ia),

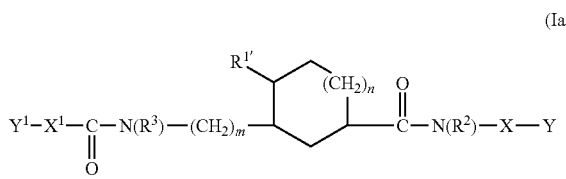

wherein X, X$^1$, Y, Y$^1$, R$^1$, R$^2$, R$^3$, m and n are as defined before. X is preferably 2-fluoro-1,4-phenylene, Y is preferably 2-oxo-1-pyridyl, 2-oxo-1-pyrazinyl or 3-oxo-4-morpholinyl, especially 2-oxo-1-pyridyl, Y$^1$—X$^1$— forms preferably 5-chloro-2-thienyl, n is preferably 0, R$^{1'}$ is hydroxy, C$_{1-6}$ alkoxy or fluoro C$_{1-6}$ alkoxy, especially hydroxy, methoxy, ethoxy or 2,2-difluoroethoxy.

x) Other preferred compounds of the invention are compounds of formula (I), where R$^{1'''}$ is hydrogen.

xi) Particularly preferred compounds of the present invention are:

5-Chloro-thiophene-2-carboxylic acid {(1S,2S,4R)-4-[2-fluoro-4-(2-oxo-2H-pyridin-1-yl)-phenylcarbamoyl]-2-hydroxy-cyclopentyl}-amide, 5-Chloro-thiophene-2-carboxylic acid {(1S,2S,4S)-4-[2-fluoro-4-(2-oxo-2H-pyridin-1-yl)-phenylcarbamoyl]-2-hydroxy-cyclopentyl}-amide, 5-Chloro-thiophene-2-carboxylic acid {(1S,2S,4R)-2-hydroxy-4-[4-(3-oxo-morpholin-4-yl)-phenylcarbamoyl]-cyclopentyl}-amide, 5-Chloro-thiophene-2-carboxylic acid {(1S,2S,4R)-4-[2-fluoro-4-(3-oxo-morpholin-4-yl)-phenylcarbamoyl]-2-hydroxy-cyclopentyl}-amide, 5-Chloro-thiophene-2-carboxylic acid {(1S,2S,4R)-4-[2-fluoro-4-(2-oxo-2H-pyrazin-1-yl)-phenylcarbamoyl]-2-hydroxy-cyclopentyl}-amide, 5-Chloro-thiophene-2-carboxylic acid {(1S,2S,4R)-2-hydroxy-4-[4-(2-oxo-2H-pyrazin-1-yl)-phenylcarbamoyl]-cyclopentyl}-amide, 5-Chloro-thiophene-2-carboxylic acid {(1S,2S,4R)-2-hydroxy-4-[2-methyl-4-(2-oxo-2H-pyridin-1-yl)-phenylcarbamoyl]-cyclopentyl}-amide, 5-Chloro-thiophene-2-carboxylic acid {(1S,2S,4R)-2-hydroxy-4-[4-(2-oxo-2H-pyridin-1-yl)-phenylcarbamoyl]-cyclopentyl}-amide, 5-Chloro-thiophene-2-carboxylic acid {(1S,2S,4R)-4-[2-fluoro-4-(2-oxo-pyrrolidin-1-yl)-phenylcarbamoyl]-2-hydroxy-cyclopentyl}-amide, Thiophene-2-carboxylic acid {(1S,2S,4R)-4-[2-fluoro-4-(2-oxo-2H-pyridin-1-yl)-phenylcarbamoyl]-2-hydroxy-cyclopentyl}-amide, 5-Chloro-thiophene-2-carboxylic acid {(1S,2S,4R)-4-[2-fluoro-4-(2-oxo-2H-pyridin-1-yl)-phenylcarbamoyl]-2-methoxy-cyclopentyl}-amide, 5-Chloro-thiophene-2-carboxylic acid {(1S,2S,4S)-4-[2-fluoro-4-(2-oxo-2H-pyridin-1-yl)-phenylcarbamoyl]-2-methoxy-cyclopentyl}-amide, 5-Chloro-thiophene-2-carboxylic acid {(1S,2S,4R)-2-(2,2-difluoro-ethoxy)-4-[2-fluoro-4-(2-oxo-2H-pyridin-1-yl)-phenylcarbamoyl]-cyclopentyl}-amide, 5-Chloro-thiophene-2-carboxylic acid {(1S,2S,4S)-2-(2,2-difluoro-ethoxy)-4-[2-fluoro-4-(2-oxo-2H-pyridin-1-yl)-phenylcarbamoyl]-cyclopentyl}-amide, 5-Chloro-thiophene-2-carboxylic acid {(1S,2S,4R)-2-ethoxy-4-[2-fluoro-4-(2-oxo-2H-pyridin-1-yl)-phenylcarbamoyl]-cyclopentyl}-amide, 5-Chloro-thiophene-2-carboxylic acid {(1SR,2RS,4SR)-4-[2-fluoro-4-(2-oxo-2H-pyridin-1-yl)-phenylcarbamoyl]-2-hydroxy-cyclopentylmethyl}-amide, 5-Chloro-thiophene-2-carboxylic acid {(1RS,2SR,4SR)-4-[2-fluoro-4-(2-oxo-2H-pyridin-1-yl)-phenylcarbamoyl]-2-hydroxy-cyclopentylmethyl}-amide, 5-Chloro-thiophene-2-carboxylic acid {(1R,2S,4S)-4-[2-fluoro-4-(2-oxo-2H-pyridin-1-yl)-phenylcarbamoyl]-2-hydroxy-cyclopentylmethyl}-amide, 5-Chloro-thiophene-2-carboxylic acid {(1S,2R,4R)-4-[2-fluoro-4-(2-oxo-2H-pyridin-1-yl)-phenylcarbamoyl]-2-hydroxy-cyclopentylmethyl}-amide, 5-Chloro-thiophene-2-carboxylic acid {(1RS,2SR,4SR)-2-hydroxy-4-[4-(3-oxo-morpholin-4-yl)-phenylcarbamoyl]-cyclopentylmethyl}-amide, 5-Chloro-thiophene-2-carboxylic acid {(1RS,2SR,4SR)-4-[2-fluoro-4-(2-oxo-2H-pyrazin-1-yl)-phenylcarbamoyl]-2-hydroxy-cyclopentylmethyl}-amide and 5-Chloro-thiophene-2-carboxylic acid {(1RS,2SR,4SR)-4-[2-fluoro-4-(3-oxo-morpholin-4-yl)-phenylcarbamoyl]-2-hydroxy-cyclopentylmethyl}-amide.

The compounds of the present invention can be prepared, for example, by the general synthetic procedures described below.

General Synthetic Procedures

Abbreviations

BOP: Benzotriazolyl-N-oxy-tris(dimethylamino)-phosphonium hexafluorophosphate

BOP-Cl: Bis-(2-oxo-3-oxazolidinyl)-phosphinic acid chloride

DIPEA: Diisopropyl ethyl amine

DMA: N,N-Dimethylacetamide

DMF: N,N-Dimethylformamide

DMSO: Dimethylsulfoxide

EDCI: N-(3-Dimetylaminopropyl)-N'-ethyl-carbodiimide hydrochloride

HOBT: 1-Hydroxybenzotriazole

PyBOP: Benzotriazol-1-yl-oxytripyrrolidinephosphonium hexafluorophosphate

TEA: Triethylamine

TBTU: O-(Benzotriazol-1-yl)-N,N,N',N'-tetramethyluronium terafluoroborate

TFA: Trifluoroacetic acid

THF: Tetrahydrofurane

Synthesis of Hydroxy-Substituted 3-aminocyclopentane carboxamides
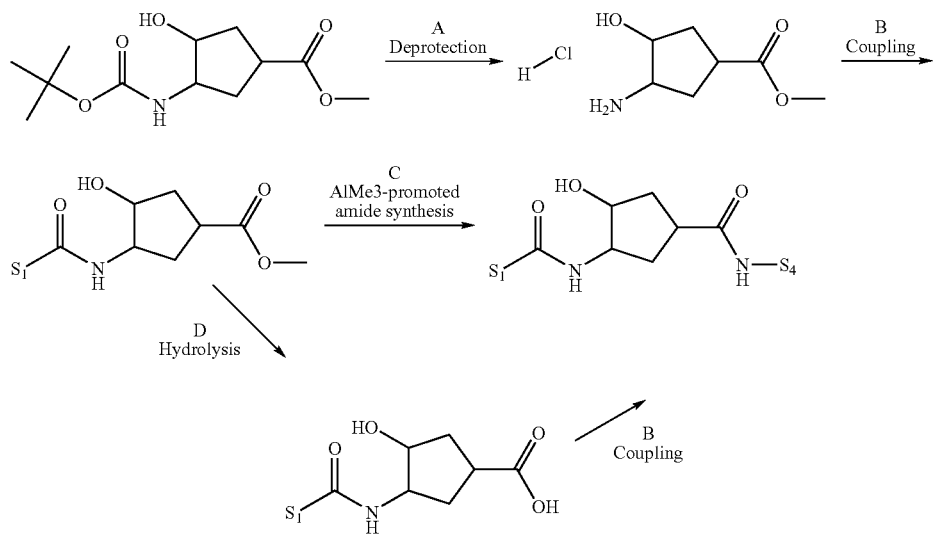
$S_1$ means $Y^1$—$X^1$—, wherein $X^1$ and $Y^1$ are as defined before, and $S_4$ means —X—Y, wherein X and Y are as defined before.
Synthesis of Alkoxy-Substituted 3-aminocyclopentane carboxamides
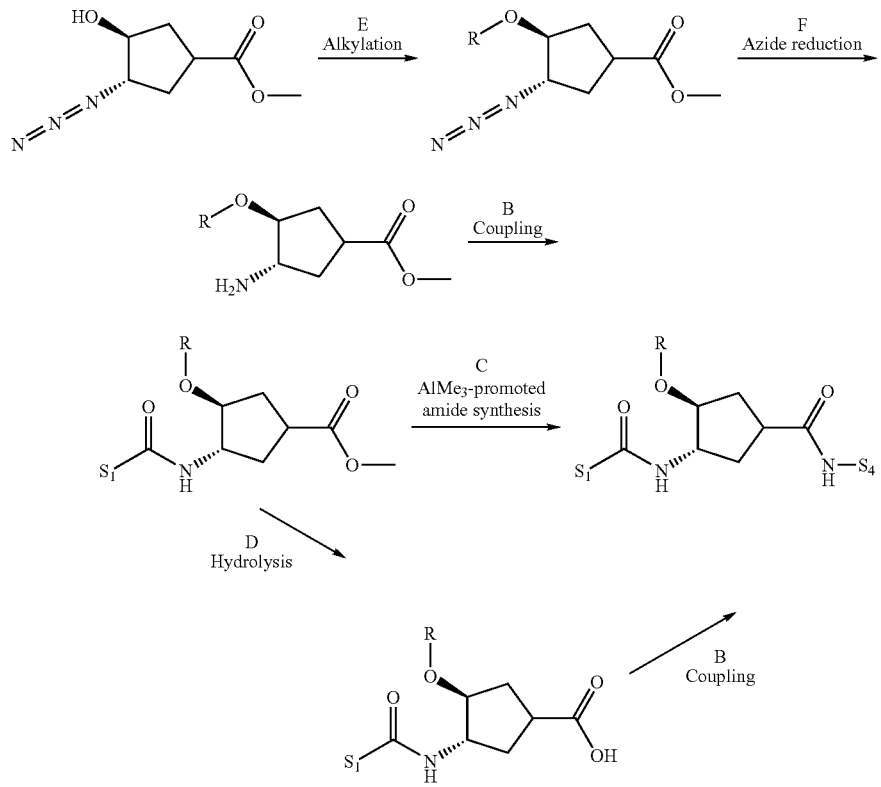

$S_1$ means $Y^1$—$X^1$—, wherein $X^1$ and $Y^1$ are as defined before, and $S_4$ means —X—Y, wherein X and Y are as defined before. R means $C_{1-6}$ alkyl or fluoro $C_{1-6}$ alkyl.

Synthesis of Hydroxy-Substituted
3-aminomethylcyclopentane carboxamides

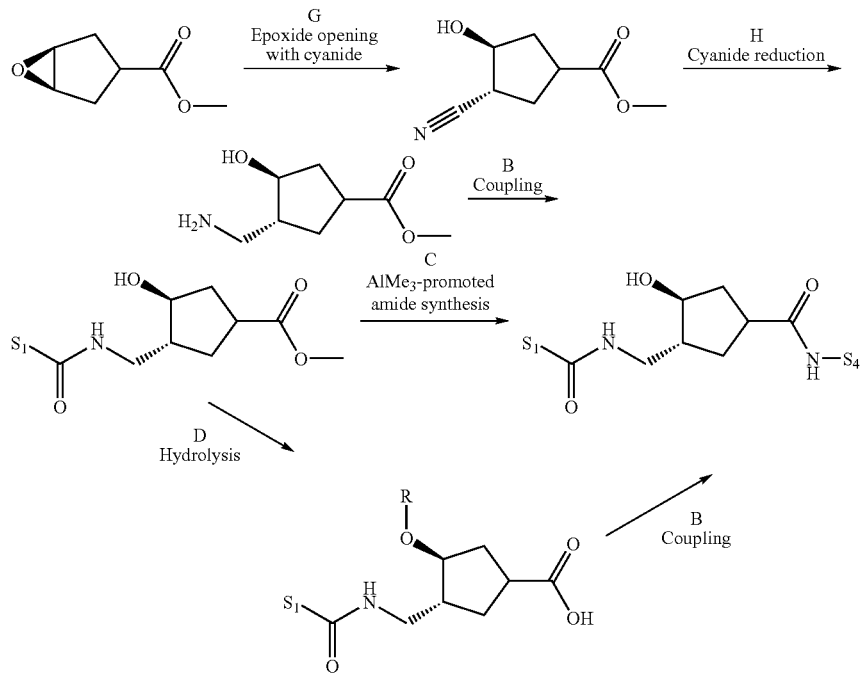

$S_1$ means $Y^1$—$X^1$—, wherein $X^1$ and $Y^1$ are as defined before, and $S_4$ means —X—Y, wherein X and Y are as defined before. R means $C_{1-6}$ alkyl or fluoro $C_{1-6}$-alkyl.

A: Deprotection of a Boc-Protected Amine

Cleavage of a Boc protecting group is effected by treatment with a mineral acid such as HCl, HBr, $H_2SO_4$ or $H_3PO_4$ or a carbonic acid such as trifluoroacetic acid, in a solvent such as $CH_2Cl_2$, dioxane or HOAc at 0 to 60° C. Preferred conditions are 4N HCl in dioxane at r.t.

B: Amide Coupling

Amide couplings are carried out in a solvent such as $CH_2Cl_2$, DMF, acetonitrile, THF or mixtures thereof. Activation is effected by an amide coupling reagent such as BOP, BOP-Cl, TBTU, EDCI, EDCI/DMAP and an additive such as HOBT, N-hydroxysuccinimide or N-hydroxy-2-pyridone in the presence of a base like TEA, DIPEA, N-methylmorpholine etc. at 0° C. to 100° C. Reaction times ranged from 1 hr to 72 hrs. Preferred conditions are DMF, BOP and DIPEA.

C: Conversion of a Carboxylic Acid Ester to an Aryl Amide Using $AlMe_3$ Activation The aniline is preactivated with $AlMe_3$ in a solvent such as toluene or dioxane under an argon atmosphere at r.t. for 1 hr-3 hrs and subsequently treated with the ester at elevated temperature (usually 90° C.-110° C.) for 1 hr-18 hrs to give the amide.

D: Hydrolysis of a Carboxylic Acid Ester

Ester hydrolysis is effected by dissolving it in a suitable solvent like MeOH, EtOH, THF, 1,4-dioxane, water or mixtures thereof and a base like LiOH, NaOH, KOH, $Na_2CO_3$, $K_2CO_3$ or $Cs_2CO_3$. Preferred conditions are NaOH in EtOH/$H_2O$.

E: Alkylation of a Hydroxyl Group

Hydroxy groups can be alkylated with an appropriate alkyl halide either by promoting the reaction with $Ag(I)_2O$ in a solvent such as toluene, THF or acetonitrile. Elevated temperatures up the boiling point of the respective solvents, multiple addition of alkyl halide and prolonged reaction times up to 6 days might be required in order to drive the reaction to completion Alternatively, the alcohol can be deprotonated with treatment with sodium hydride in DMF for 1 hr and then reacted with an appropriate alkyl halide or triflate for 1 hr-48 hrs.

F: Reduction of an Azide to the Corresponding Amine

Azides are converted to the corresponding amines by hydrogenation under normal pressure or by transfer hydrogenation with a catalyst such as $PtO_2$, Pd—C or Raney nickel in solvents such as MeOH, EtOH, $H_2O$, dioxane, THF, HOAc or mixtures thereof. Alternatively, azides can be converted to the corresponding amines by treatment with triphenylphosphine in $H_2O$/THF. Preferred conditions are hydrogenation with hydrogen in the presence of $PtO_2$ in MeOH as solvent.

G: Epoxide Opening with Cyanide

Epoxides converted to the corresponding 1,2-cyanohydrine by reaction with a cyanide salt such as LiCN, NaCN or KCN in polar solvent such as DMSO, DMF, THF, water or mixtures thereof using additives such as $LiClO_4$, $Ti(OiPr)_4$, $B(OEt)_3$ or HCl. Alternatively, they can be reacted with trimethylsilyl cyanide in polar inert solvents such as $CH_2Cl_2$ or $MeNO_2$ using a Lewis acid additives such as $AlCl_3$ or $BF_3$—$OEt_2$. The conversion can also be effected using diethylaluminium cyanide in toluene. The latter conditions are preferred.

H: Reduction of a Cyanide to the Corresponding Aminomethyl Derivative

Cyanides are hydrogenated under normal or elevated pressure or by transfer hydrogenation with a catalyst such as $PtO_2$ or Pd—C or reduced with diborane in solvents such as MeOH, EtOH, $H_2O$, dioxane, THF, HOAc or mixtures thereof. Preferred conditions are hydrogenation with hydrogen under normal pressure in the presence of $PtO_2$ in EtOH as solvent.

As described above, the compounds of formula (I) are active compounds and inhibit the coagulation factor Xa. These compounds consequently influence both platelet activation which is induced by this factor and plasmatic blood coagulation. They therefore inhibit the formation of thrombi and can be used for the treatment and/or prevention of thrombotic disorders, such as, amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. The compounds of the present invention can also be used in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumor agents.

Prevention and/or treatment of thrombotic disorders, particularly arterial or deep vein thrombosis, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of diseases which are associated with the coagulation factor Xa, particularly as therapeutically active substances for the treatment and/or prophylaxis of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour.

In another preferred embodiment, the invention relates to a method for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour, which method comprises administering a compound as defined above to a human being or animal.

The invention also embraces the use of compounds as defined above for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour.

The invention also relates to the use of compounds as described above for the preparation of medicaments for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour. Such medicaments comprise a compound as described above.

The invention also relates to the process and the intermediates for manufacturing the compounds of formula (I) as well as the process for manufacturing the intermediates.

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Example AA

The inhibition of the coagulation factor Xa by the compounds of the present invention can be demonstrated with the aid of a chromogenic peptide substrate assay as described hereinafter.

Factor Xa activity was measured spectrophotometrically in microtiter plates in a final volume of 150 µl using the following conditions: Inhibition of human factor Xa (Enzyme Research Laboratories) was tested at an enzyme concentration of 3 nM using the chromogenic substrate S-2222 (Chromogenix AB, Mölndal, Sweden) at 200 nM. The reaction kinetics of the enzyme and the substrate were linear with both time and the enzyme concentration. The inhibitors were dissolved in DMSO and tested at various concentrations up to 100 µM. The inhibitors were diluted using HNPT buffer consisting of HEPES 100 mM, NaCl 140 mM, PEG 6000 0.1% and Tween 80 0.02%, pH 7.8. The cleavage of S-2222 by human factor Xa was followed at 405 nm for 5 minutes at room temperature. The velocity of the reaction was determined by the autoreader from the slope of the linear regression fit to 7 time points (1 minute). The initial velocity for each inhibitor concentration was determined by the slope of at least 4 time points in the linear phase by a linear regression fit (mOD/min$^2$). Apparent dissociation constants $K_i$ were calculated according to Cheng and Prusoff [Cheng, Y. C.; Prusoff, W. H. Relationship between the inhibition constant ($K_i$) and the concentration of the inhibitor that causes 50 percent inhibition ($IC_{50}$) of an enzyme reaction. Biochem. Pharmacol. 1973, 22, 3099-3108.] based on the $IC_{50}$ and the respective $K_m$, determined previously ($K_i=IC_{50}/(1+S/K_m)$). The $K_m$ for the substrate used was determined under the conditions of the test with at least 5 substrate concentrations ranging from 0.5 to 15 times $K_m$. [Lottenberg R, Hall J A, Blinder M, Binder E P, Jackson C M., The action of thrombin on peptide p-nitroanilide substrates. Substrate selectivity and examination of hydrolysis under different reaction conditions. Biochim Biophys Acta. 1983 Feb. 15; 742(3):539-57]. According to Eadie [Eadie G. S. The inhibition of cholinesterase by physostigmine and prostigmine. J. Biol. Chem. 1942, 146, 85-93.], the $K_m$ for S-2222 amounted to 613 µM.

The activity of the low molecular weight substances can, moreover, be characterized in the "prothrombin time" (PT) clotting test. The substances are prepared as a 10 mM solution in DMSO and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 µl of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 µl of plasma/inhibitor mixture in the measurement container. The clotting reaction was initiated by the addition of 0.1 ml of Dade® Innovin® (recombinant human tissue factor combined with calcium buffer and synthetic phospholipids, Dade Behring, Inc., Cat. B4212-50). The time up to the fibrin cross-linking was determined photooptically from the ACL. The inhibitor concentration, which brought about a doubling of the PT clotting time, was determined by fitting the data to an exponential regression (XLfit).

The compounds of the present invention can furthermore be characterised by the Activated Partial Thromboplastin time (aPTT). This coagulation test can e.g. be run on the ACL 300 Coagulation System (Instrumentation Laboratory) automatic analyzer. The substances are prepared as a 10 mM solution in DMSO and thereafter made up to the desired dilution in the same solvent. The test is performed with the Dade® Actin® FS Activated PTT reagent (purified soy phosphatides in 1.0×10$^{-4}$M ellagic acid, stabilizers and preservative, Dade Behring, Inc., Cat. B4218-100). Thereafter, 0.25 ml aliquots of human plasma (obtained from whole blood anticoagulated with 1/10 volume of 108 mM Na citrate) are spiked with 5 µl of test compound in at least 6 concentrations. 50 µl plasma at 4° C. containing 1/50 vol. inhibitor in solvent are incubated with 50 µl Dade® Actin® FS Activated PTT reagent in water at 37° C. for 3 min., then 50 µl CaCl$_2$.2H$_2$O 25 mM in water at 37° C. are added. The time up to the fibrin cross-linking was determined photooptically from the ACL. The inhibitor concentration, which brought about a doubling of the APTT clotting time, was determined by fitting the data to an exponential regression (XLfit).

The $K_i$ values of the active compounds of the present invention preferably amount to about 0.001 to 50 µM, especially about 0.001 to 1 µM. The PT values preferably amount to about 0.5 to 100 µM, especially to about 0.5 to 10 µM. The aPTT values preferably amount to about 0.5 to 100 µM, especially to about 0.5 to 10 µM.

| Example | $K_i$ [µM] factor Xa |
| --- | --- |
| Example 1C | 0.015 |
| Example 5 | 0.018 |
| Example 13B | 0.006 |
| Example 15C | 0.030 |

Example 1

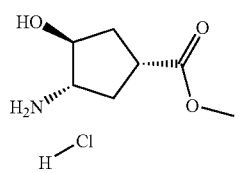

1A

A solution of (1S,2S,4R)—N—Boc-1-amino-2-hydroxy-cyclopentane-4-carboxylic acid methyl ester (0.2 g) in 4M HCl in dioxane (4 ml) was stirred under an argon atmosphere at r.t. for 2 hrs. The reaction mixture was concentrated to give (1R,3S,4S)-3-amino-4-hydroxy-cyclopentanecarboxylic acid methyl ester hydrochloride (165 mg, contains some dioxane) as light brown gum. MS: 160.4 ([M+H]$^+$).

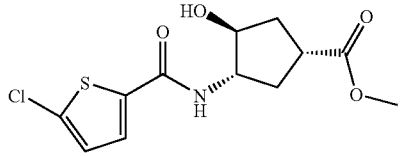

1B

A solution of (1R,3S,4S)-3-amino-4-hydroxy-cyclopentanecarboxylic acid methyl ester hydrochloride (160 mg) in THF (5 ml) was treated under an argon atmosphere with N-ethyldiisopropylamine (0.56 ml), 5-chloro-2-thiophenecarboxylic acid (160 mg) and BOP (434 mg). The mixture soon turned to a clear light yellow solution and was then stirred for 18 h. The reaction mixture was concentrated. The crude product was purified by chromatography (silica gel; gradient: cyclohexane→cyclohexane/EtOAc 3:7) to give (1R,3S,4S)-3-[(5-chloro-thiophene-2-carbonyl)-amino]-4-hydroxy-cyclopentane-carboxylic acid methyl ester as colorless gum. MS: 304.0 ([M+H]$^+$).

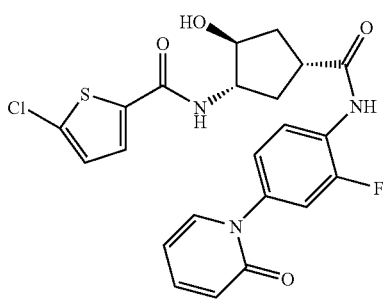

1C

To a stirred suspension of 1-(4-amino-3-fluoro-phenyl)-1H-pyridin-2-one (296 mg; CAS 536747-52-1, prepared according to C. F. Bigge et al., patent application WO 2003045912) at r.t. in dioxane (3 ml) under an argon atmosphere was added carefully trimethyl aluminium solution (0.72 ml; 2M in heptane). After stirring for 2 hrs at r.t., a solution of (1R,3S,4S)-3-[(5-chloro-thiophene-2-carbonyl)-amino]-4-hydroxy-cyclopentane-carboxylic acid methyl ester (110 mg) in dioxane (3 ml) was added. The mixture was heated to 100° C. and stirring at that temperature was continued for 24 h. The mixture was cooled to r.t. and water (0.8 ml) was added. After 15 min stirring, MgSO$_4$ was added and stirring was continued for another 15 min. The solids were filtered off and washed with dichloromethane. The filtrate was concentrated. The crude product was isolated by column chromatography (silica gel; gradient: CH$_2$Cl$_2$→CH$_2$Cl$_2$/MeOH 9:1) to give 5-chloro-thiophene-2-carboxylic acid {(1S,2S,4R)-4-[2-fluoro-4-(2-oxo-2H-pyridin-1-yl)-phenylcarbamoyl]-2-hydroxy-cyclopentyl}-amide (81 mg) as light yellow solid. MS: 476.0 ([M+H]$^+$).

Example 2

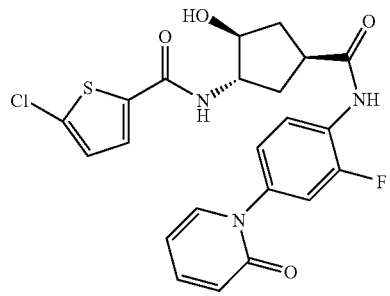

In analogy to example 1, (1S,2S,4S)—N—Boc-1-amino-2-hydroxycyclopentane-4-carboxylic acid methyl ester (CAS 321744-19-8) was converted to 5-chloro-thiophene-2-carboxylic acid {(1S,2S,4S)-4-[2-fluoro-4-(2-oxo-2H-pyridin-1-yl)-phenylcarbamoyl]-2-hydroxy-cyclopentyl}-amide. Light yellow solid. MS 476.0 ([M+H]$^+$)

Example 3

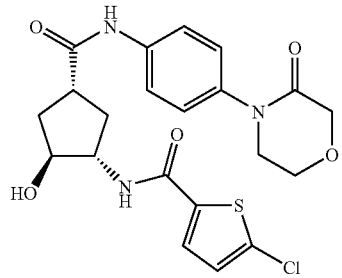

In analogy to example 1C, (1R,3S,4S)-3-[(5-chloro-thiophene-2-carbonyl)-amino]-4-hydroxy-cyclopentanecarboxylic acid methyl ester (example 1B) was reacted with 4-(4-amino-phenyl)-morpholin-3-one (CAS 438056-69-0) to give 5-chloro-thiophene-2-carboxylic acid {(1S,2S,4R)-2-hydroxy-4-[4-(3-oxo-morpholin-4-yl)-phenylcarbamoyl]-cyclopentyl}-amide. Yellow solid. MS: 464.4 ([M+H]$^+$)

Example 4

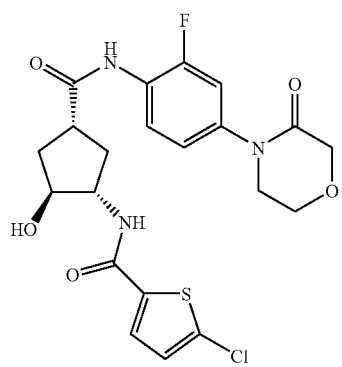

In analogy to example 1C, (1R,3S,4S)-3-[(5-chloro-thiophene-2-carbonyl)-amino]-4-hydroxy-cyclopentanecarboxylic acid methyl ester (example 1B) was reacted with 4-(4-amino-3-fluoro-phenyl)-morpholin-3-one (CAS 438056-69-0) to give 5-chloro-thiophene-2-carboxylic acid {(1S,2S,4R)-4-[2-fluoro-4-(3-oxo-morpholin-4-yl)-phenyl-carbamoyl]-2-hydroxy-cyclo-pentyl}-amide. Yellow solid. MS: 482.3 ([M+H]⁺)

Example 5

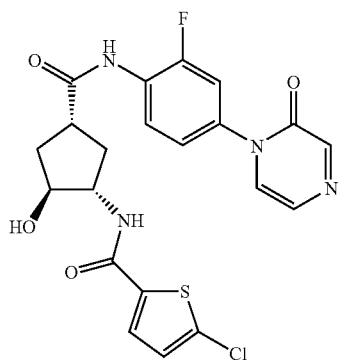

In analogy to example 1C, (1R,3S,4S)-3-[(5-chloro-thiophene-2-carbonyl)-amino]-4-hydroxy-cyclopentanecarboxylic acid methyl ester (example 1B) was reacted with 1-(4-amino-3-fluoro-phenyl)-1H-pyrazin-2-one (prepared from 2-fluoro-4-iodoaniline by reaction with 1H-pyrazin-2-one, Cu(I)I, N,N'-dimethylethylenediamine and cesium carbonate in dioxane at 120° C.) to give 5-chloro-thiophene-2-carboxylic acid {(1S,2S,4R)-4-[2-fluoro-4-(2-oxo-2H-pyrazin-1-yl)-phenylcarbamoyl]-2-hydroxy-cyclopentyl}-amide. Yellow solid. MS: 477.0 ([M+H]⁺)

Example 6

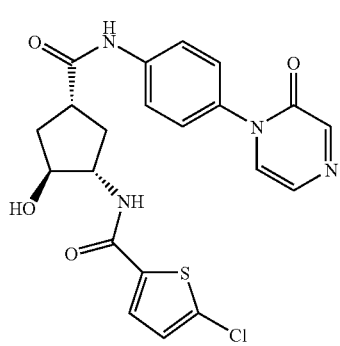

In analogy to example 1C, (1R,3S,4S)-3-[(5-chloro-thiophene-2-carbonyl)-amino]-4-hydroxy-cyclopentanecarboxylic acid methyl ester (example 1B) was reacted with 1-(4-aminophenyl)-1H-pyrazin-2-one (CAS 444002-64-6) to give 5-chloro-thiophene-2-carboxylic acid {(1S,2S,4R)-2-hydroxy-4-[4-(2-oxo-2H-pyrazin-1-yl)-phenylcarbamoyl]-cyclopentyl}-amide. Light yellow solid. MS: 459.3 ([M+H]⁺)

Example 7

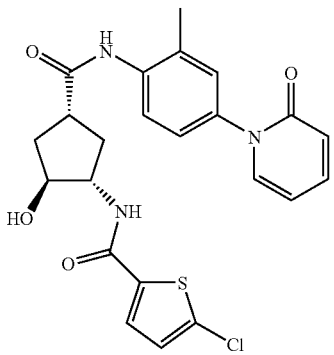

In analogy to example 1C, (1R,3S,4S)-3-[(5-chloro-thiophene-2-carbonyl)-amino]-4-hydroxy-cyclopentanecarboxylic acid methyl ester (example 1B) was reacted with 1-(4-amino-3-methyl-phenyl)-1H-pyridin-2-one to give 5-chloro-thiophene-2-carboxylic acid {(1S,2S,4R)-2-hydroxy-4-[2-methyl-4-(2-oxo-2H-pyridin-1-yl)-phenylcarbamoyl]-cyclopentyl}-amide. Off-white solid. MS: 472.4 ([M+H]⁺).

Example 8

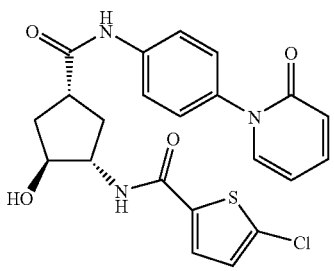

In analogy to example 1C, (1R,3S,4S)-3-[(5-chloro-thiophene-2-carbonyl)-amino]-4-hydroxy-cyclopentanecarboxylic acid methyl ester (example 1B) was reacted with 1-(4-amino-phenyl)-1H-pyridin-2-one (CAS 13143-47-0) to give 5-chloro-thiophene-2-carboxylic acid {(1S,2S,4R)-2-hydroxy-4-[4-(2-oxo-2H-pyridin-1-yl)-phenyl-carbamoyl]-cyclopentyl}-amide. Orange solid. MS: 458.3 ([M+H]⁺).

Example 9

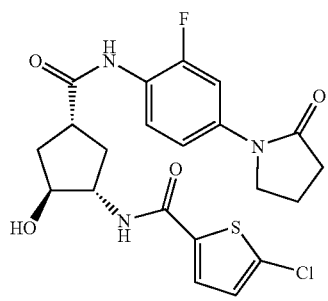

In analogy to example 1C, (1R,3S,4S)-3-[(5-chloro-thiophene-2-carbonyl)-amino]-4-hydroxy-cyclopentanecarboxylic acid methyl ester (example 1B) was reacted with 1-(4-amino-3-fluoro-phenyl)-pyrrolidin-2-one (prepared from 2-fluoro-4-iodoaniline with 2-pyrrolidinone, CuI, ethylendiamine and K$_3$PO$_4$ in refluxing 1,4-dioxane).to give 5-chloro-thiophene-2-carboxylic acid {(1S,2S,4R)-2-hydroxy-4-[2-methyl-4-(2-oxo-2H-pyridin-1-yl)-phenylcarbamoyl]-cyclopentyl}-amide. Orange solid. MS: 466.0 ([M+H]$^+$).

Example 10

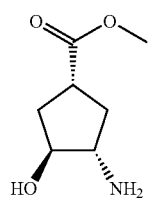

10A

To a stirred solution of (1R,3S,4S)-3-azido-4-hydroxy-cyclopentanecarboxylic acid methyl ester (2.73 g; CAS 213742-85-9; prepared as described in WO00/09463) at r.t. in methanol (30 ml) was added under an argon atmosphere Pt$_2$O (140 mg). The reaction mixture was hydrogenated over night. The catalyst was filtered off and washed with MeOH. The filtrate was concentrated to give (1R,3S,4S)-3-amino-4-hydroxy-cyclopentanecarboxylic acid methyl ester (2.29 g) as brown oil. MS: 160.3 ([M+H]$^+$).

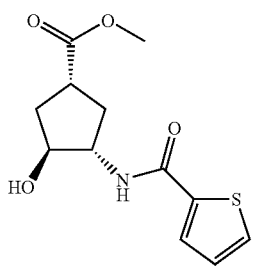

10B

To a stirred solution of the (1R,3S,4S)-3-amino-4-hydroxy-cyclopentanecarboxylic acid methyl ester (300 mg) at r.t. in DMF (7.0 ml) under an argon atmosphere were added N-ethyldiisopropylmine (0.96 ml), 2-thiophene carboxylic acid (314 mg) and BOP (1.04 g). The mixture was then stirred at r.t. for 19 h. The clear brown solution was diluted with EtOAc and washed with H$_2$O. The aqueous phase was back extracted with EtOAc. The combined organics were washed with H$_2$O and brine, dried (MgSO$_4$), filtered and concentrated. The crude product was purified by column chromatography (silica gel; gradient: cyclohexane→cyclohexane/EtOAc 1:1) to give (1R,3S,4S)-3-hydroxy-4-[(thiophene-2-carbonyl)-amino]-cyclopentanecarboxylic acid methyl ester as light brown gum. MS: 270.3 ([M+H]$^+$).

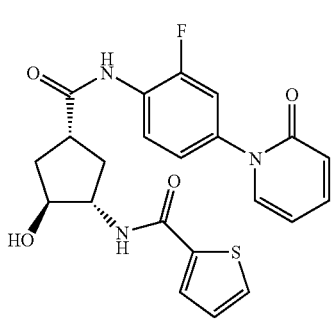

10C

In analogy to example 1C, 1R,3S,4S)-3-hydroxy-4-[(thiophene-2-carbonyl)-amino]-cyclo-pentanecarboxylic acid methyl ester was reacted with 1-(4-amino-3-fluoro-phenyl)-1H-pyridin-2-one (CAS 536747-52-1, prepared according to C. F. Bigge et al., patent application WO 2003045912) to give thiophene-2-carboxylic acid {(1S,2S,4R)-4-[2-fluoro-4-(2-oxo-2H-pyridin-1-yl)-phenylcarbamoyl]-2-hydroxy-cyclopentyl}-amide. Light yellow solid. MS: 442.1 ([M+H]$^+$).

Example 11

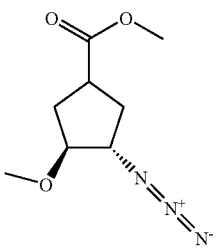

11A

To a stirred, cooled (0° C.) solution of (1R,3S,4S)-3-azido-4-hydroxy-cyclopentanecarboxylic acid methyl ester (300 mg; CAS 213742-85-9) in DMF (5 ml) under an argon atmosphere was added NaH (78 mg; 55% dispersion in mineral oil). The ice bath was removed and stirring at r.t. was continued for 1 h. The mixture was cooled again and methyl iodide (0.3 ml) was added in one portion. The mixture (slowly warming up to r.t.) was then stirred for 18 h. More methyl iodide (0.3 ml) was added and the mixture (orange slurry) was stirred at r.t. for another 7 h. More methyl iodide (0.3 ml) was added and stirring was continued for another 17 h. The mixture was diluted with EtOAc and washed with H$_2$O (10 ml). The aqueous phase was back extracted with EtOAc. The combined organics were washed with H$_2$O and brine, dried (MgSO$_4$), filtered and concentrated. The crude product was purified by column chromatography (silica gel; gradient: cyclohexane→cyclohexane/EtOAc 65:35) to give (3S,4S)-3-azido-4-methoxy-cyclopentanecarboxylic acid methyl ester (215 mg, epimeric mixture) as light yellow oil. MS: 200.3 ([M+H]$^+$).

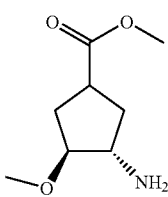

11B

In analogy to example 10A, (3S,4S)-3-azido-4-methoxy-cyclopentanecarboxylic acid methyl ester was hydrogenated to give (3S,4S)-3-amino-4-methoxy-cyclopentanecarboxylic acid methyl ester. Colorless viscous oil. MS 174.1 ([M+H]$^+$)

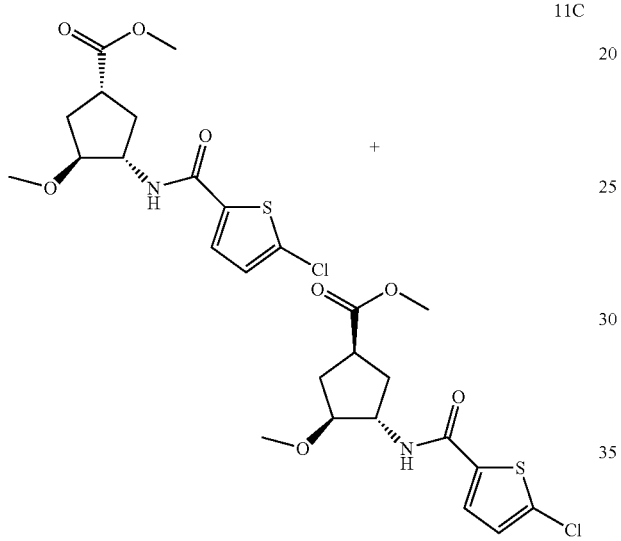

11C

+

In analogy to example 10B, (3S,4S)-3-amino-4-methoxy-cyclopentanecarboxylic acid methyl ester was coupled with 5-chloro-2-thiophenecarboxylic acid. The epimers were separated by column chromatography (silica gel; gradient: cyclohexane→cyclohexane/EtOAc 65:35) to give (1R,3S, 4S)-3-[(5-chloro-thiophene-2-carbonyl)-amino]-4-methoxy-cyclopentanecarboxylic acid methyl ester and (1S,3S, 4S)-3-[(5-chloro-thiophene-2-carbonyl)-amino]-4-methoxy-cyclopentanecarboxylic acid methyl ester, both as off-white solids. MS: 318.0 ([M+H]$^+$).

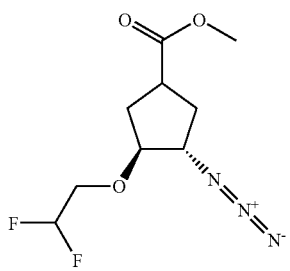

11D

In analogy to example 1C, (1R,3S,4S)-3-[(5-chloro-thiophene-2-carbonyl)-amino]-4-methoxy-cyclopentanecarboxylic acid methyl ester was reacted with 1-(4-amino-3-fluoro-phenyl)-1H-pyridin-2-one to give 5-chloro-thiophene-2-carboxylic acid {(1S,2S,4R)-4-[2-fluoro-4-(2-oxo-2H-pyridin-1-yl)-phenylcarbamoyl]-2-methoxy-cyclopentyl}-amide. Light yellow amorphous solid. MS: 490.1 ([M+H]$^+$).

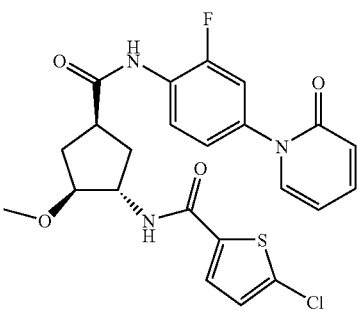

11E

In analogy to example 1C, (1S,3S,4S)-3-[(5-chloro-thiophene-2-carbonyl)-amino]-4-methoxy-cyclopentanecarboxylic acid methyl ester was reacted with 1-(4-amino-3-fluoro-phenyl)-1H-pyridin-2-one to give 5-chloro-thiophene-2-carboxylic acid {(1S,2S,4S)-4-[2-fluoro-4-(2-oxo-2H-pyridin-1-yl)-phenylcarbamoyl]-2-methoxy-cyclopentyl}-amide. Yellow solid. MS: 490.0 ([M+H]$^+$).

Example 12

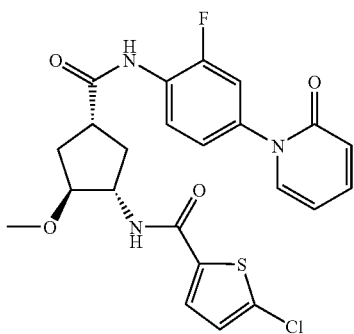

12A

To a stirred suspension of NaH (259 mg; 55% dispersion in mineral oil) at 0° C. in DMF (5 ml) under an argon atmosphere was added a solution of (1R,3S,4S)-3-azido-4-hydroxy-cyclopentanecarboxylic acid methyl ester (1.0 g) in DMF (5 ml). The ice bath was removed and stirring at r.t. was continued for 1 h. The brown mixture was cooled again in an ice bath and 2,2-difluoroethyl trifluoromethanesulfonate (2.31 g) was added in one portion. The ice bath was removed and stirring at r.t. was continued for 19 h. The mixture was diluted with EtOAc and washed with H$_2$O. The aqueous phase was back extracted with EtOAc. The combined organics were washed with H$_2$O and brine, dried (MgSO$_4$), filtered and concentrated. The crude product was isolated by column chromatography (silica gel; gradient: cyclohexane→cyclohexane/EtOAc 65:35) to give (3S,4S)-3-azido-4-(2,2-difluoro-ethoxy)-cyclopentane-carboxylic acid methyl ester (746 mg) as colorless oil. MS: 250.2 ([M+H]$^+$).

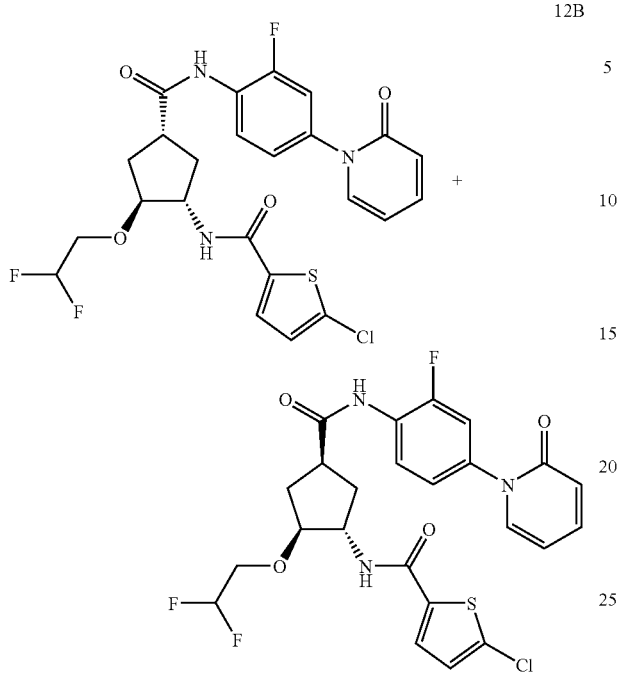

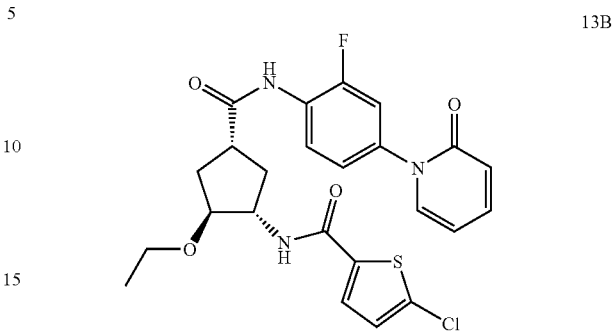

In analogy to examples 11B-E, (3S,4S)-3-azido-4-(2,2-difluoro-ethoxy)-cyclopentanecarboxylic acid methyl ester was converted to 5-chloro-thiophene-2-carboxylic acid {(1S,2S,4R)-2-(2,2-difluoro-ethoxy)-4-[2-fluoro-4-(2-oxo-2H-pyridin-1-yl)-phenylcarbamoyl]-cyclopentyl}-amide and 5-chloro-thiophene-2-carboxylic acid {(1S,2S,4S)-2-(2,2-difluoro-ethoxy)-4-[2-fluoro-4-(2-oxo-2H-pyridin-1-yl)-phenylcarba-moyl]-cyclopentyl}-amide, both compounds as orange solids. MS: 540.2/540.3 ([M+H]$^+$).

The epimeric mixture was separated by chromatography on silica gel after the coupling of the aminocyclopentane intermediate with 5-chloro-2-thiophenecarboxylic acid.

Example 13

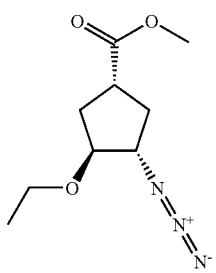

To a stirred solution of (1R,3S,4S)-3-azido-4-hydroxy-cyclopentanecarboxylic acid methyl ester (500 mg) at r.t. in acetonitrile/THF 3:1 (8 ml) under an argon atmosphere were added Ag$_2$O (1.88 g) and ethyl iodide (2.18 ml). The black suspension was stirred for 18 h at 60° C., then cooled to r.t. The black solid was filtered off and washed with ethyl acetate. The filtrate was concentrated. The crude product was purified by column chromatography (silica gel; gradient: cyclohexane→cyclohexane/EtOAc 7:3) to give (1R,3S,4S)-3-azido-4-ethoxy-cyclopentanecarboxylic acid methyl ester (474 mg) as light yellow oil. MS: 214.1 ([M+H]$^+$).

In analogy to examples 11B-D, (1R,3S,4S)-3-azido-4-ethoxy-cyclopentanecarboxylic acid methyl ester was converted to 5-chloro-thiophene-2-carboxylic acid {(1S,2S,4R)-2-ethoxy-4-[2-fluoro-4-(2-oxo-2H-pyridin-1-yl)-phenylcarbamoyl]-cyclopentyl}-amide. Light brown solid. MS: 504.8 ([M+H]$^+$).

Example 14

14A

To a stirred, cooled (0° C.) solution of trans-6-oxa-bicyclo[3.1.0]hexane-3-carboxylic acid methyl ester (1 g; CAS 86885-57-6) in toluene (9 ml) under an argon atmosphere was added diethylaluminim cyanide (7.7 ml; 1 M solution in toluene) over a period of 5 min. When addition was complete, the ice bath was removed and the clear light yellow solution (slowly warming up to room temperature) was then stirred for 24 h.

The mixture was cooled in an ice bath, diluted with EtOAc (8 ml) and sodium fluoride was added in 2 portions portionwise over a period of 5 min. H$_2$O (1 ml) was then added to the mixture→foaming. The evolving HCN was trapped into a 1 N NaOH aqueous solution. After 30 min stirring, the mixture was filtered through a pad of MgSO$_4$. The cake was rinsed 3 times with EtOAc. The filtrate was concentrated. The crude product was purified by column chromatography (silica gel; gradient: cyclohexane→cyclohexane/EtOAc 3:1) to give (1SR,3SR,4RS)-3-cyano-4-hydroxy-cyclopentanecarboxylic acid methyl ester (482 mg) as light brown oil. MS: 170.1 ([M+H]$^+$).

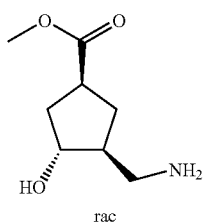

14B rac

To a stirred solution of (1SR,3SR,4RS)-3-cyano-4-hydroxy-cyclopentanecarboxylic acid methyl ester (185 mg) at r.t. in methanol (5 ml) under an argon atmosphere were added benzyl chloride (0.38 ml) and 10% Pd/C (50 mg). The mixture was stirred at r.t. under a hydrogen atmosphere (balloon) overnight. The catalyst was filtered off and washed with methanol. The filtrate was concentrated to leave a brown viscous oil. This was taken up in 10 ml sat. aq. NaHCO$_3$ and extracted with CH$_2$Cl$_2$/MeOH 9:1 (3×10 ml) and CH$_2$Cl$_2$/MeOH 4:1 (10 ml). A white solid started to precipitate out of the biphasic mixture which was filtered off. The filtrate was neutralized by the addition of 1 N HCl and concentrated to leave crude (1SR,3SR,4RS)-3-aminomethyl-4-hydroxy-cyclopentane-carboxylic acid methyl ester as a light brown solid (189 mg).

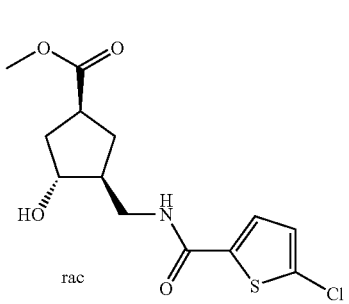

14C rac

To a stirred suspension of the crude (1SR,3SR,4RS)-3-aminomethyl-4-hydroxy-cyclopentanecarboxylic acid methyl ester (189 mg) at r.t. in DMF (5 ml) under an argon atmosphere were added N-ethyldiisopropylamine (0.74 ml), BOP (531 mg) and 5-chloro-2-thiophenecarboxylic acid (195 mg). The reaction mixture was stirred over night, then diluted with EtOAc and washed with H$_2$O. The aqueous phase was back extracted with EtOAc. The combined organics were washed with H$_2$O and brine, dried (MgSO$_4$), filtered and concentrated. The crude product was purified by column chromatography (silica gel; gradient: CH$_2$Cl$_2$→CH$_2$Cl$_2$/MeOH 93:7) to give (1SR,3SR,4RS)-3-{[(5-chloro-thiophene-2-carbonyl)-amino]-methyl}-4-hydroxy-cyclopentanecarboxylic acid methyl ester (111 mg) as light brown gum. MS: 318.0 ([M+H]$^+$).

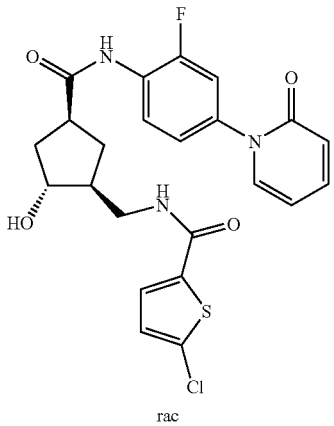

14D rac

In analogy to example 1C, (1SR,3RS,4SR)-3-{[(5-chloro-thiophene-2-carbonyl)-amino]-methyl}-4-hydroxy-(1SR,3SR,4RS)-3-{[(5-chloro-thiophene-2-carbonyl)-amino]-methyl}-4-hydroxy-cyclopentanecarboxylic acid methyl ester was reacted with 1-(4-amino-3-fluoro-phenyl)-1H-pyridin-2-one (CAS 536747-52-1, prepared according to C. F. Bigge et al., patent application WO 2003045912) to give 5-chloro-thiophene-2-carboxylic acid {(1SR,2RS,4SR)-4-[2-fluoro-4-(2-oxo-2H-pyridin-1-yl)-phenylcarbamoyl]-2-hydroxy-cyclopentylmethyl}-amide. Orange solid. MS: 490.0 ([M+H]$^+$).

Example 15

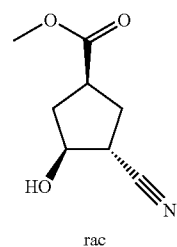

15A rac

To a stirred, cooled (ice bath) solution of cis-6-oxa-bicyclo[3.1.0]hexane-3-carboxylic acid methyl ester (5.41 g; CAS 86941-00-6) in toluene (45 ml) under an argon atmosphere was added diethylaluminium cyanide (41.7 ml; 1 M solution in toluene) over a period of 10 min. When addition was complete, the mixture (slowly warming up to room temperature) was stirred at r.t. for 22 h. The light yellow clear solution was diluted with toluene (35 ml), cooled in an ice bath and NaF (42.0 g) was added in 2 portions, followed by H$_2$O (6 ml) over a period of 5 min→strong foaming. The evolving HCN was trapped in a 1 N NaOH solution. After 10 min, the ice bath was removed and the mixture (light yellow compact slurry) was stirred at r.t. for another 30 min. The mixture was filtered and the cake was rinsed with plenty of toluene. The filtrate was concentrated. The crude product was purified by column chromatography (silica gel; gradient: cyclohexane→cyclohexane/EtOAc 35:65) to give (1SR,3RS,4SR)-3-cyano-4-hydroxy-cyclopentane-carboxylic acid methyl ester (3.91 g) as light yellow oil.

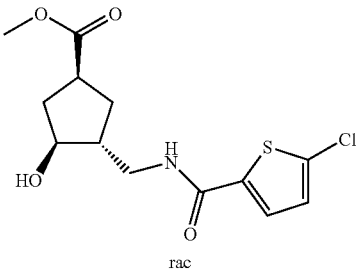

In analogy to example 14B and 14C (1SR,3RS,4SR)-3-cyano-4-hydroxy-cyclopentanecarboxylic acid methyl ester was converted to (1SR,3RS,4SR)-3-{[(5-chloro-thiophene-2-carbonyl)-amino]-methyl}-4-hydroxy-cyclopentanecarboxylic acid methyl ester. Light brown gum. MS: 318.1 ([M+H]+).

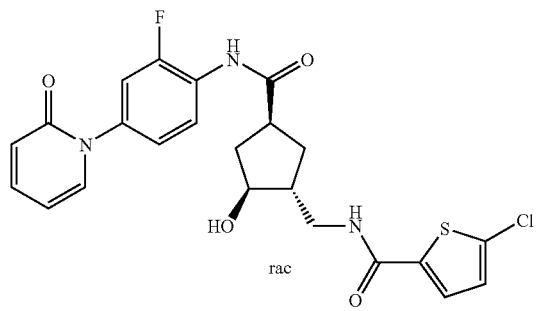

In analogy to example 1C, (1SR,3RS,4SR)-3-{[(5-chloro-thiophene-2-carbonyl)-amino]-methyl}-4-hydroxy-cyclopentanecarboxylic acid methyl ester was reacted with 1-(4-amino-3-fluoro-phenyl)-1H-pyridin-2-one (CAS 536747-52-1, prepared according to C. F. Bigge et al., patent application WO 2003045912) to give 5-chloro-thiophene-2-carboxylic acid (1RS,2SR,4SR)-4-[2-fluoro-4-(2-oxo-2H-pyridin-1-yl)-phenylcarbamoyl]-2-hydroxy-cyclopentylmethyl}-amide. Orange solid. MS: 490.0 ([M+H]+).

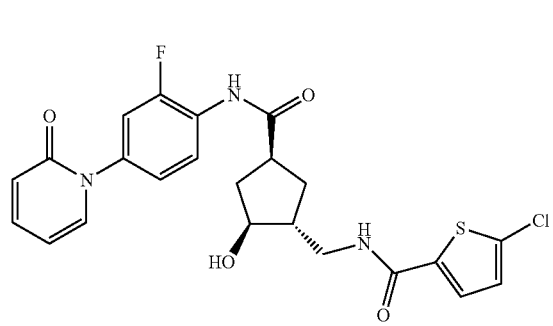

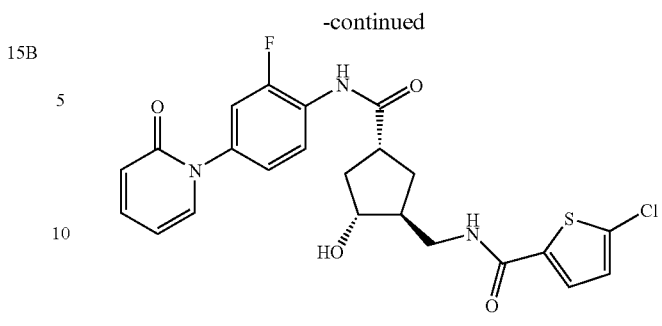

The racemic 5-chloro-thiophene-2-carboxylic acid {(1RS,2SR,4SR)-4-[2-fluoro-4-(2-oxo-2H-pyridin-1-yl)-phenylcarbamoyl]-2-hydroxy-cyclopentylmethyl}-amide (143 mg) was separated into its enantiomers by HPLC on a chiral stationary phase (Chiralcel OD; eluent: 20% EtOH in heptane) to give 5-chloro-thiophene-2-carboxylic acid {(1R,2S,4S)-4-[2-fluoro-4-(2-oxo-2H-pyridin-1-yl)-phenylcarbamoyl]-2-hydroxy-cyclopentylmethyl}-amide and 5-chloro-thiophene-2-carboxylic acid {(1S,2R,4R)-4-[2-fluoro-4-(2-oxo-2H-pyridin-1-yl)-phenylcarbamoyl]-2-hydroxy-cyclopentylmethyl}-amide, both as off-white solids. MS: 490.1/490.4 ([M+H]+).

Example 16

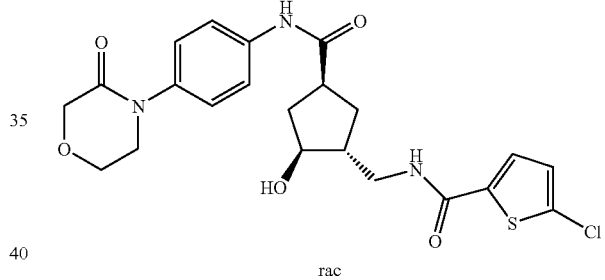

In analogy to example 15C, (1SR,3RS,4SR)-3-{[(5-chloro-thiophene-2-carbonyl)-amino]-methyl}-4-hydroxy-cyclopentanecarboxylic acid methyl ester was reacted with 4-(4-amino-phenyl)-morpholin-3-one (CAS 438056-69-0) to give 5-chloro-thiophene-2-carboxylic acid {(1RS,2SR,4SR)-2-hydroxy-4-[4-(3-oxo-morpholin-4-yl)-phenylcarbamoyl]-cyclopentylmethyl}-amide. Orange solid. MS: 478.3 ([M+H]+).

Example 17

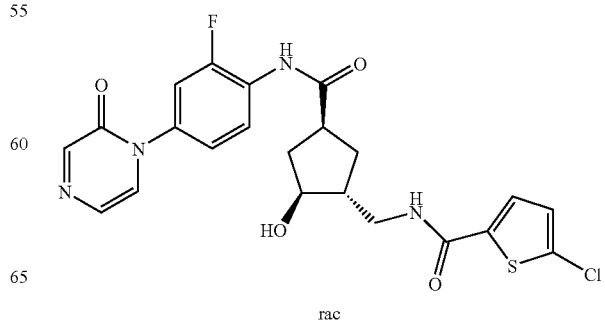

In analogy to example 21C, (1SR,3RS,4SR)-3-{[(5-chloro-thiophene-2-carbonyl)-amino]-methyl}-4-hydroxy-cyclopentanecarboxylic acid methyl ester was reacted with 1-(4-amino-3-fluoro-phenyl)-1H-pyrazin-2-one (prepared from 2-fluoro-4-iodoaniline by reaction with 1H-pyrazin-2-one, Cu(I)I, N,N'-dimethylethylenediamine and cesium carbonate in dioxane at 120° C.) to give 5-chloro-thiophene-2-carboxylic acid {(1RS,2SR,4SR)-4-[2-fluoro-4-(2-oxo-2H-pyrazin-1-yl)-phenylcarbamoyl]-2-hydroxy-cyclopentylmethyl}-amide. Orange solid. MS: 491.3. ([M+H]$^+$).

Example 18

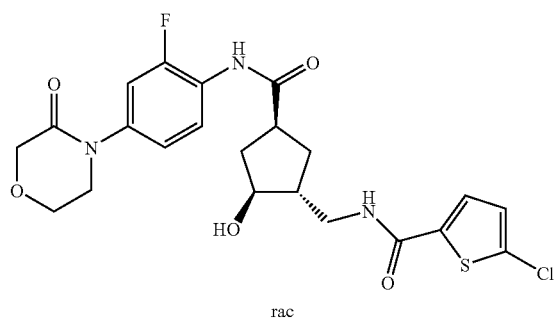

rac

In analogy to example 21C, (1SR,3RS,4SR)-3-{[(5-chloro-thiophene-2-carbonyl)-amino]-methyl}-4-hydroxy-cyclopentanecarboxylic acid methyl ester was reacted with 4-(4-amino-3-fluoro-phenyl)-morpholin-3-one (CAS 438056-69-0) to give 5-chloro-thiophene-2-carboxylic acid {(1RS,2SR,4SR)-4-[2-fluoro-4-(3-oxo-morpholin-4-yl)-phenylcarbamoyl]-2-hydroxy-cyclopentylmethyl}-amide. Orange solid. MS: 496.3. ([M+H]$^+$).

Example 19

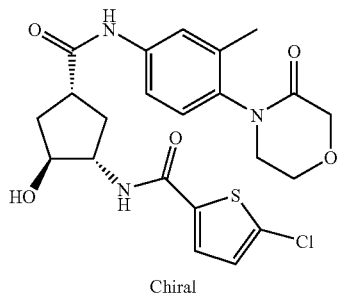

Chiral

In analogy to example 1C, (1R,3S,4S)-3-[(5-chloro-thiophene-2-carbonyl)-amino]-4-hydroxy-cyclopentanecarboxylic acid methyl ester (example 1B) was reacted with 1-(4-amino-2-methyl-phenyl)-3-morpholinone (CAS 482308-10-1) to give 5-chloro-thiophene-2-carboxylic acid {(1S,2S,4R)-2-hydroxy-4-[3-methyl-4-(3-oxo-morpholin-4-yl)-phenylcarbamoyl]-cyclopentyl}-amide. Off-white solid. MS: 478.4 ([M+H]$^+$).

Example 20

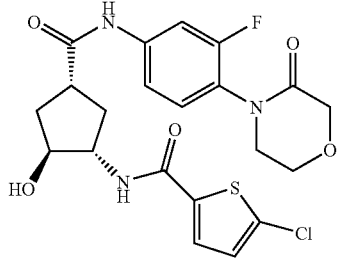

In analogy to example 1C, (1R,3S,4S)-3-[(5-chloro-thiophene-2-carbonyl)-amino]-4-hydroxy-cyclopentanecarboxylic acid methyl ester (example 1B) was reacted with 1-(4-amino-2-fluoro-phenyl)-3-morpholinone (CAS 482308-19-0) to give 5-chloro-thiophene-2-carboxylic acid {(1S,2S,4R)-4-[3-fluoro-4-(3-oxo-morpholin-4-yl)-phenylcarbamoyl]-2-hydroxy-cyclopentyl}-amide. Orange solid. MS: 482.5 ([M+H]$^+$).

Example 21

21A

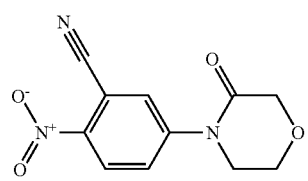

A suspension of 5-chloro-2-nitrobenzonitrile (2.41 g), morpholin-3-one (2 g), cesium carbonate (6.45 g), tris(dibenzylideneacetone)dipalladium (120 mg) and 4,5-bis(diphenylphosphino)-9,9-dimethylxanthene (230 mg) in dioxane (30 ml) was heated overnight at 120° C. The reaction mixture was cooled, diluted with CH$_2$Cl$_2$ and filtered through decalite. Extraction (water and brine) and chromatography (silica gel, AcOEt) delivered 2-nitro-5-(3-oxo-morpholin-4-yl)-benzonitrile as a yellow solid (1.77 g). MS: 248.3 ([M+H]$^+$).

21B

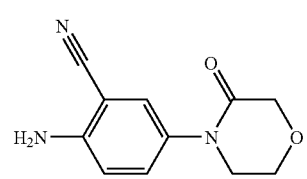

A solution of 2-nitro-5-(3-oxo-morpholin-4-yl)-benzonitrile (1.1 g) in THF (80 ml) was hydrogenated at 1 atm in the presence of Pd/C 10% (350 mg) at room temperature. The reaction mixture was filtered through decalite and precipitated (AcOEt/heptane) to yield 2-amino-5-(3-oxo-morpholin-4-yl)-benzonitrile as a white solid (580 mg). MS: 218.4 ([M+H]$^+$).

Example 22

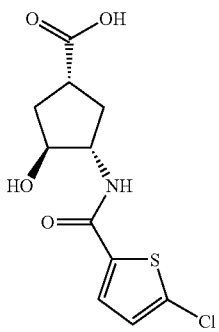

21C

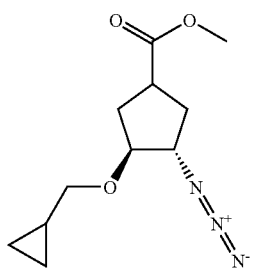

22A

To a stirred suspension of (1R,3S,4S)-3-[(5-chloro-thiophene-2-carbonyl)-amino]-4-hydroxy-cyclopentanecarboxylic acid methyl ester (611 mg; example 1B) in MeOH (4 ml) was added 1N NaOH (4 ml). The reaction mixture which slowly turned into a clear solution was stirred at r.t. for 2 hrs, then concentrated. The residue was dissolved in $H_2O$ and washed with $Et_2O$. The aqueous phase was acidified with 3N HCl, then extracted with $CH_2Cl_2$/MeOH 9:1. The combined organic layers were washed with $H_2O$ and brine, dried over $MgSO_4$ and concentrated to give (1R,3S,4S)-3-[(5-chloro-thiophene-2-carbonyl)-amino]-4-hydroxy-cyclopentanecarboxylic acid (442 mg) as off-white solid. MS: 288.0 ([M−H]$^-$).

In analogy to example 11A (1R,3S,4S)-3-azido-4-hydroxy-cyclopentanecarboxylic acid methyl ester (CAS 213742-85-9) was reacted with (bromomethyl)cyclopropane to give (3S,4S)-3-azido-4-cyclopropylmethoxy-cyclopentanecarboxylic acid methyl ester. Colorless oil.

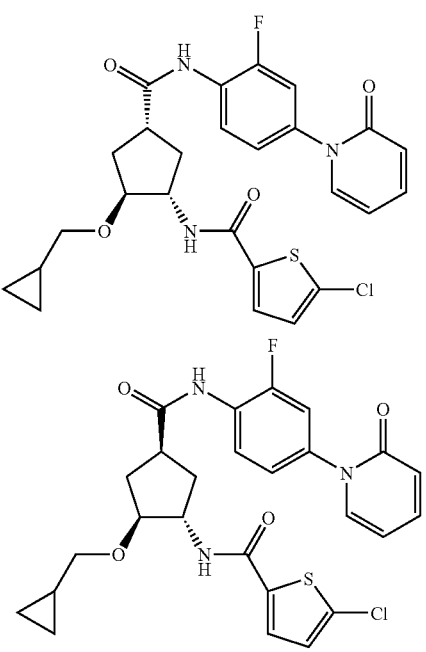

22B

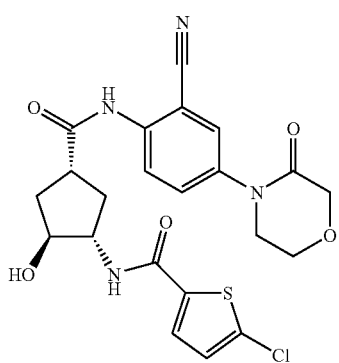

21D

To a stirred suspension of 2-amino-5-(3-oxo-morpholin-4-yl)-benzonitrile (114 mg; example 21B) in acetonitrile/DMF 9:1 (5 ml) were added triethylamine (0.22 ml), (1R,3S,4S)-3-[(5-chloro-thiophene-2-carbonyl)-amino]-4-hydroxy-cyclopentanecarboxylic acid (198 mg) and BOP-Cl (174 mg). The reaction mixture was stirred at 80° C. overnight, then cooled to r.t. and concentrated. The crude product was purified by column chromatography (silica gel; gradient: $CH_2Cl_2 \rightarrow CH_2Cl_2$/MeOH 9:1) to give 5-chloro-thiophene-2-carboxylic acid {(1S,2S,4R)-4-[2-cyano-4-(3-oxo-morpholin-4-yl)-phenylcarbamoyl]-2-hydroxy-cyclopentyl}-amide (6 mg). Off-white solid. MS: 489.0 ([M+H]$^+$).

In analogy to example 11B-E (3S,4S)-3-azido-4-cyclopropylmethoxy-cyclopentanecarboxylic acid methyl ester was converted to 5-chloro-thiophene-2-carboxylic acid {(1S,2S,4R)-2-cyclopropylmethoxy-4-[2-fluoro-4-(2-oxo-2H-pyridin-1-yl)-phenylcarbamoyl]-cyclopentyl}-amide and 5-chloro-thiophene-2-carboxylic acid {(1S,2S,4S)-2-cyclopropylmethoxy-4-[2-fluoro-4-(2-oxo-2H-pyridin-1-yl)-phenylcarbamoyl]-cyclopentyl}-amide, both as light yellow amorphous solid. MS: 530.3 ([M+H]$^+$). The epimeric mixture was separated by chromatography on silica gel after the coupling of the aminocyclopentane intermediate with 5-chloro-2-thiophenecarboxylic acid.

Example 23

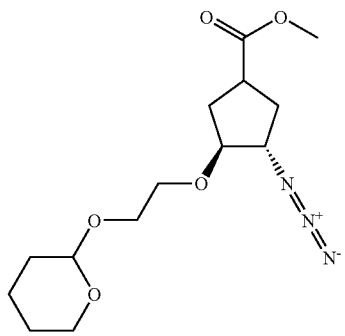

23A

In analogy to example 11A (1R,3S,4S)-3-azido-4-hydroxy-cyclopentanecarboxylic acid methyl ester (CAS 213742-85-9) was reacted with 2-(2-bromoethoxy)tetrahydro-2H-pyran to give (3S,4S)-3-azido-4-[2-(tetrahydro-pyran-2-yloxy)-ethoxy]-cyclopentanecarboxylic acid methyl ester. Light yellow oil. MS 336.3 ([M+H]$^+$).

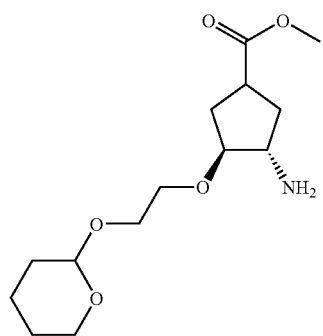

23B

In analogy to example 10A and example 1B, (S,4S)-3-azido-4-[2-(tetrahydro-pyran-2-yloxy)-ethoxy]-cyclopentanecarboxylic acid methyl ester was hydrogenated in the presence of PtO$_2$ and coupled with 5-chloro-2-thiophenecarboxylic acid to give (3S,4S)-3-[(5-chloro-thiophene-2-carbonyl)-amino]-4-[2-(tetrahydro-pyran-2-yloxy)-ethoxy]-cyclopentanecarboxylic acid methyl ester. Brown gum. MS 432.2 ([M+H]$^+$).

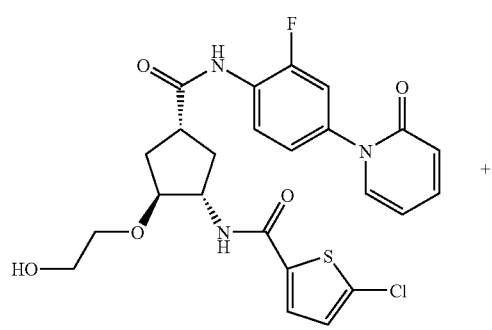

23C

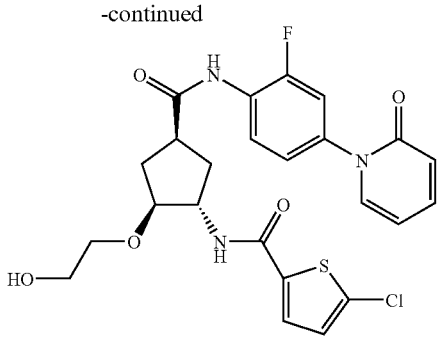

To a stirred solution of (3S,4S)-3-[(5-chloro-thiophene-2-carbonyl)-amino]-4-[2-(tetrahydro-pyran-2-yloxy)-ethoxy]-cyclopentanecarboxylic acid methyl ester (175 mg) in dioxane (3 ml) was added 4M HCl (2 ml). The reaction mixture was stirred at 40° C. for overnight, then concentrated and used in the next step without further purification.

In analogy to example 1C the crude product was reacted with 1-(4-amino-3-fluoro-phenyl)-1H-pyridin-2-one (336 mg; CAS 536747-52-1, prepared according to C. F. Bigge et al., patent application WO 2003045912) to give 5-chloro-thiophene-2-carboxylic acid [(1S,2S,4R)-4-[2-fluoro-4-(2-oxo-2H-pyridin-1-yl)-phenylcarbamoyl]-2-(2-hydroxy-ethoxy)-cyclopentyl]-amide (14 mg) and 5-chloro-thiophene-2-carboxylic acid [(1S,2S,4S)-4-[2-fluoro-4-(2-oxo-2H-pyridin-1-yl)-phenylcarbamoyl]-2-(2-hydroxy-ethoxy)-cyclopentyl]-amide (9 mg), both as light yellow amorphous solid. MS 520.3 ([M+H]$^+$). The epimeric mixture was separated by chromatography on silica gel after the final step.

Example 24

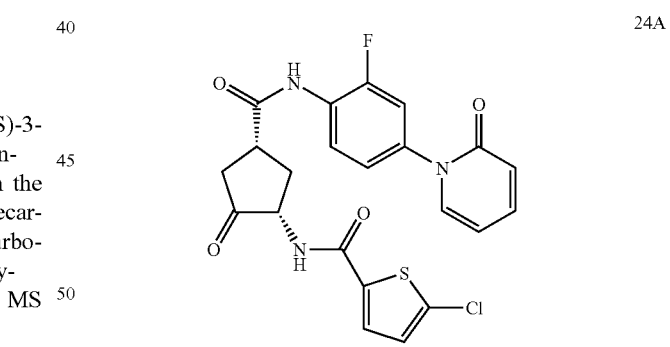

24A

To a stirred solution of 5-chloro-thiophene-2-carboxylic acid {(1S,2S,4R)-4-[2-fluoro-4-(2-oxo-2H-pyridin-1-yl)-phenylcarbamoyl]-2-hydroxy-cyclopentyl}-amide (318 mg; example 1C) in DMSO/CH$_2$Cl$_2$ 1:1 (6 ml) were added triethylamine (0.73 ml) and SO$_3$-pyridine complex (638 mg). The mixture was stirred overnight at r.t. The clear brown solution was diluted with dichloromethane, washed with 0.5 N HCl, H$_2$O and brine, dried over MgSO$_4$, filtered and concentrated. The crude product was purified by column chromatography (silica gel; gradient: CH$_2$Cl$_2$→CH$_2$Cl$_2$/MeOH 95:5) to give 5-chloro-thiophene-2-carboxylic acid {(1S,4R)-4-[2-fluoro-4-(2-oxo-2H-pyridin-1-yl)-phenylcarbamoyl]-2-oxo-cyclopentyl}-amide (225 mg) as light yellow amorphous solid. MS 474.1 ([M+H]$^+$).

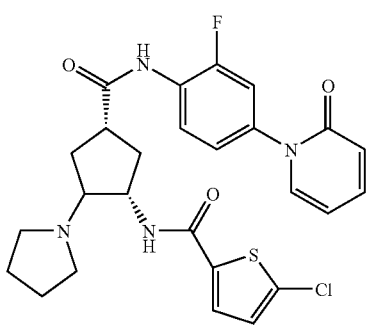

24B

To a stirred solution of 5-chloro-thiophene-2-carboxylic acid {(1S,4R)-4-[2-fluoro-4-(2-oxo-2H-pyridin-1-yl)-phenylcarbamoyl]-2-oxo-cyclopentyl}-amide (75 mg) in THF (3 ml) were added pyrrolidine (0.03 ml) and acetic acid (0.02 ml). After stirring for 1 hr at r.t., NaBH₃CN (11 mg) was added and stirring of the yellow reaction mixture was continued over night, then concentrated. The crude product was purified by column chromatography (silica gel; gradient: CH₂Cl₂→CH₂Cl₂MeOH 85:15) to give 5-chloro-thiophene-2-carboxylic acid {(1S,4R)-4-[2-fluoro-4-(2-oxo-2H-pyridin-1-yl)-phenylcarbamoyl]-2-pyrrolidin-1-yl-cyclopentyl}-amide (40 mg) as crystalline solid. MS 529.3 ([M+H]⁺).

Example 25

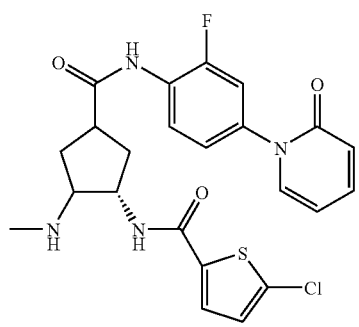

In analogy to example 24B 5-chloro-thiophene-2-carboxylic acid {(1S,4R)-4-[2-fluoro-4-(2-oxo-2H-pyridin-1-yl)-phenylcarbamoyl]-2-oxo-cyclopentyl}-amide was reacted with methylamine (using a saturated solution in THF) to give 5-chloro-thiophene-2-carboxylic acid {(S)-4-[2-fluoro-4-(2-oxo-2H-pyridin-1-yl)-phenylcarbamoyl]-2-methylamino-cyclopentyl}-amide. Crystalline white solid. MS 489.3 ([M+H]⁺).

Example 26

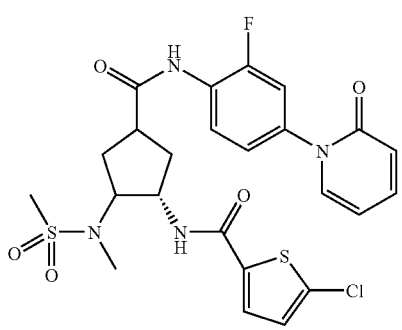

To a stirred solution of 5-chloro-thiophene-2-carboxylic acid {(S)-4-[2-fluoro-4-(2-oxo-2H-pyridin-1-yl)-phenylcarbamoyl]-2-methylamino-cyclopentyl}-amide (36 mg) in acetonitrile (2 ml) were added N-ethyldiisopropylamine (0.03 ml) and mesyl chloride (0.01 ml). The reaction mixture was stirred at r.t. for 3 hrs, then concentrated. The crude product was purified by column chromatography (silica gel; gradient: CH₂Cl₂→CH₂Cl₂/MeOH 92:8) to give 5-chloro-thiophene-2-carboxylic acid [(S)-4-[2-fluoro-4-(2-oxo-2H-pyridin-1-yl)-phenylcarbamoyl]-2-(methanesulfonyl-methyl-amino)-cyclopentyl]-amide (32 mg) as off-white solid. MS 567.2 ([M+H]⁺).

Example 27

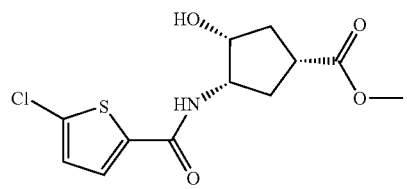

27A

In analogy to example 1A and 1B (1S,2R,4R)—N—Boc-1-amino-2-hydroxycyclopentane-4-carboxylic acid was converted to (1R,3S,4R-3-[(5-chloro-thiophene-2-carbonyl)-amino]-4-hydroxy-cyclopentanecarboxylic acid methyl ester. White solid. MS 304.0 ([M+H]⁺).

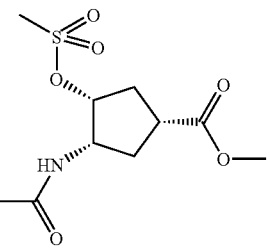

27B

A solution of (1R,3S,4R)-3-[(5-chloro-thiophene-2-carbonyl)-amino]-4-hydroxy-cyclopentane-carboxylic acid methyl ester (136 mg) in CH₂Cl₂ (5 ml) was treated at 0° C. with N-ethyl-diisopropyl amine (0.38 ml) and mesyl chloride (0.04 ml). The reaction mixture was stirred at 0° C., then diluted with H₂O and extracted with CH₂Cl₂. The organic layer was washed with H₂O, dried over MgSO₄ and concentrated. The crude product was purified by column chromatography (silica gel; gradient: CH₂Cl₂→CH₂Cl₂MeOH 95:5) to give (1R,3S,4R)-3-[(5-chloro-thiophene-2-carbonyl)-amino]-4-methanesulfonyloxy-cyclopentanecarboxylic acid methyl ester (159 mg) as off-white solid. MS 380.1 ([M−H]⁻).

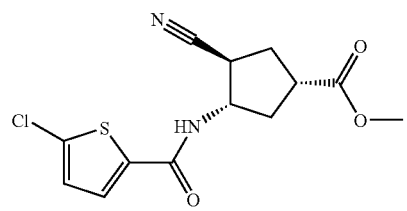

27C

A solution of (1R,3S,4R)-3-[(5-chloro-thiophene-2-carbonyl)-amino]-4-methanesulfonyloxy-cyclopentanecarboxylic acid methyl ester (150 mg) in acetonitrile (5 ml) was treated with tetraethylammonium cyanide (74 mg) and heated to reflux for 4 hrs. The reaction mixture was concentrated. The crude product was isolated by column chromatography (silica gel; gradient: CH$_2$Cl$_2$→CH$_2$Cl$_2$/MeOH 95:5) to give 3-[(5-chloro-thiophene-2-carbonyl)-amino]-4-cyano-cyclopentanecarboxylic acid methyl ester (100 mg) as light brown oil.

27D

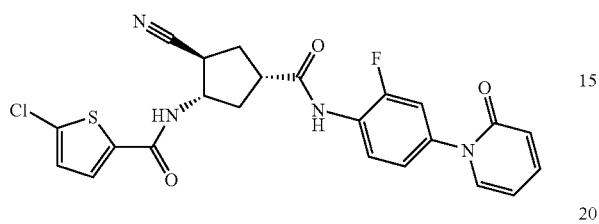

In analogy to example 1C 3-[(5-chloro-thiophene-2-carbonyl)-amino]-4-cyano-cyclopentanecarboxylic acid methyl ester was reacted with 1-(4-amino-3-fluoro-phenyl)-1H-pyridin-2-one (CAS 536747-52-1, prepared according to C. F. Bigge et al., patent application WO 2003045912) to give 5-chloro-thiophene-2-carboxylic acid {(1S,2S,4S)-2-cyano-4-[2-fluoro-4-(2-oxo-2-pyridin-1-yl)-phenylcarbamoyl]-cyclopentyl}-amide. Light yellow solid. MS 483.4 ([M−H]$^-$).

Example 28

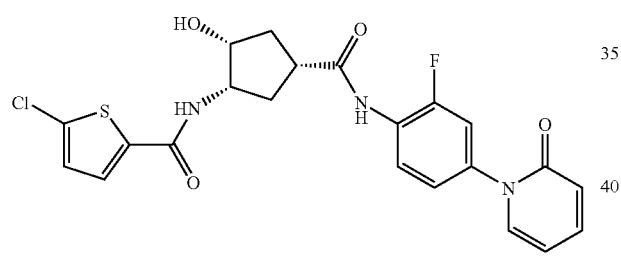

In analogy to example 1C (1R,3S,4R)-3-[(5-chloro-thiophene-2-carbonyl)-amino]-4-hydroxy-cyclopentanecarboxylic acid methyl ester was reacted with 1-(4-amino-3-fluoro-phenyl)-1H-pyridin-2-one (CAS 536747-52-1, prepared according to C. F. Bigge et al., patent application WO 2003045912) to give 5-chloro-thiophene-2-carboxylic acid {(1S,2R,4R)-4-[2-fluoro-4-(2-oxo-2-pyridin-1-yl)-phenylcarbamoyl]-2-hydroxy-cyclopentyl}-amide. Off-white solid. MS 474.0 ([M−H]$^-$).

Example 29

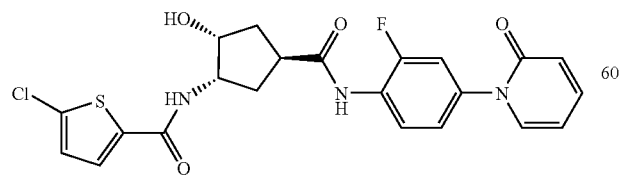

In analogy to example 1 (1S,2R,4S)—N-Boc-1-amino-2-hydrocyclopentene-4-carboxylic acid methylester was converted to 5-chloro-thiophene-2-carboxylic acid {(1S,2R,4S)-4-[2-fluoro-4-(2-oxo-2-pyridin-1-yl)-phenylcarbamoyl]-2-hydroxy-cyclopentyl}-amide. Yellow solid. MS 476.3 ([M+H]$^+$).

Example 30

30A

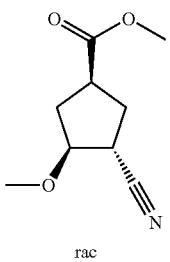

A solution of (1SR,3RS,4SR)-3-cyano-4-hydroxy-cyclopentanecarboxylic acid methyl ester (878 mg; example 15A) in THF (15 ml) was transferred to a sealed tube and treated with Ag$_2$O (3.6 g) and methyl iodide (3.23 ml) and stirred at 60° C. overnight. The reaction mixture was filtered, and the cake was rinsed with plenty of THF. The filtrate was concentrated. The crude product was purified by column chromatography (silica gel; gradient: cyclohexane→cyclohexane/EtOAc 65:35) to give (1SR,3RS,4SR)-3-cyano-4-methoxy-cyclopentanecarboxylic acid methyl ester (600 mg) as light yellow oil.

30B

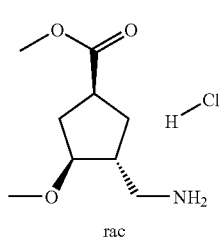

To a stirred solution of (1SR,3RS,4SR)-3-cyano-4-methoxy-cyclopentanecarboxylic acid methyl ester (595 mg) in ethanol/chloroform 5:1 (6 ml) was added PtO$_2$ (60 mg). The reaction mixture was hydrogenated overnight. The catalyst was filtered off and washed with MeOH. The filtrate was concentrated to give (1SR,3RS,4SR)-3-aminomethyl-4-methoxy-cyclopentanecarboxylic acid methyl ester hydrochloride (704 mg) as white amorphous semisolid. MS 188.3 ([M+H]$^+$).

30C

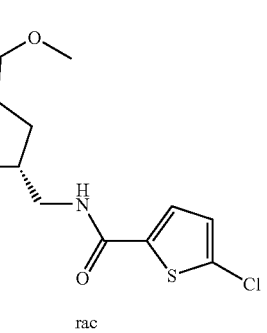

41

In analogy to example 14C (1SR,3RS,4SR)-3-aminomethyl-4-methoxy-cyclopentanecarboxylic acid methyl ester hydrochloride was reacted with 5-chloro-2-thiophenecarboxylic acid to give (1SR,3RS,4SR)-3-{[(5-chlorothiophene-2-carbonyl)-amino]-methyl}-4-methoxy-cyclopentane-carboxylic acid methyl ester. Viscous oil. MS 332.3 ([M+H]⁺).

30D

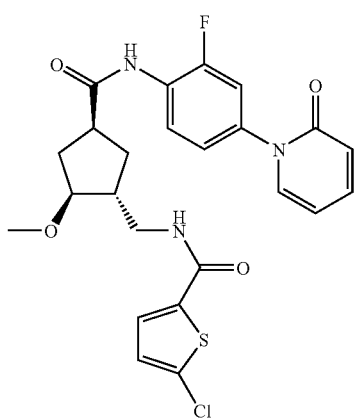

In analogy to example 1C (1SR,3RS,4SR)-3-{[(5-chlorothiophene-2-carbonyl)-amino]-methyl}-4-methoxy-cyclopentane-carboxylic acid methyl ester was converted to 5-chloro-thiophene-2-carboxylic acid {(1RS,2SR,4SR)-4-[2-fluoro-4-(2-oxo-2H-pyridin-1-yl)-phenylcarbamoyl]-2-methoxy-cyclopentylmethyl}-amide. Yellow solid. MS 504.3 ([M+H]⁺).

Example 31

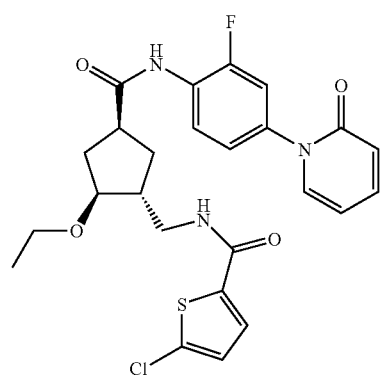

In analogy to example 30 (1SR,3RS,4SR)-3-cyano-4-hydroxy-cyclopentanecarboxylic acid methyl ester (example 15A) was converted to 5-chloro-thiophene-2-carboxylic acid {(1RS,2SR,4SR)-2-ethoxy-4-[2-fluoro-4-(2-oxo-2H-pyridin-1-yl)-phenylcarbamoyl]-cyclopentylmethyl}-amide. Yellow solid. MS 518.0 ([M+H]⁺).

42

Example 32

32A

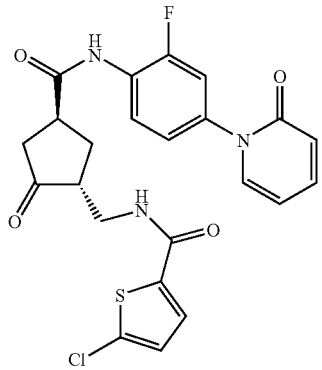

In analogy to example 24A 5-chloro-thiophene-2-carboxylic acid {(1RS,2SR,4SR)-4-[2-fluoro-4-(2-oxo-2H-pyridin-1-yl)-phenylcarbamoyl]-2-hydroxy-cyclopentylmethyl}-amide (example 15C) was oxidized to 5-chloro-thiophene-2-carboxylic acid {(1RS,4SR)-4-[2-fluoro-4-(2-oxo-2H-pyridin-1-yl)-phenylcarbamoyl]-2-oxo-cyclopentylmethyl}-amide. Light yellow foam. 488.0 ([M+H]⁺).

32B

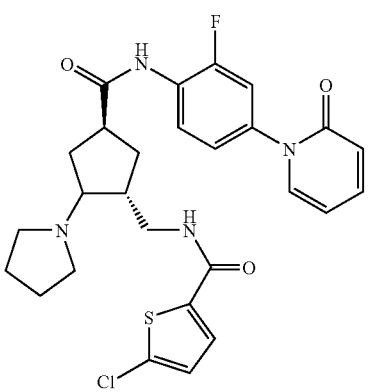

In analogy to example 24B 5-chloro-thiophene-2-carboxylic acid {(1RS,4SR)-4-[2-fluoro-4-(2-oxo-2H-pyridin-1-yl)-phenylcarbamoyl]-2-oxo-cyclopentylmethyl}-amide was reacted with pyrrolidine to give 5-chloro-thiophene-2-carboxylic acid {(1RS,4SR)-4-[2-fluoro-4-(2-oxo-2H-pyridin-1-yl)-phenylcarbamoyl]-2-pyrrolidin-1-yl-cyclopentylmethyl}-amide. Off-white crystalline solid. 543.3 ([M+H]⁺).

Example 33

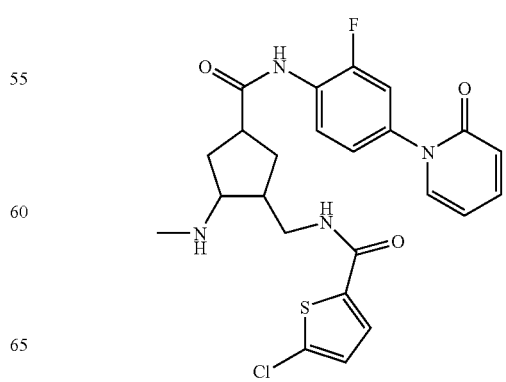

In analogy to example 25 5-chloro-thiophene-2-carboxylic acid {(1RS,4SR)-4-[2-fluoro-4-(2-oxo-2H-pyridin-1-yl)-phenylcarbamoyl]-2-oxo-cyclopentylmethyl}-amide (example 32A) was reacted with methylamine (solution in THF) to give 5-chloro-thiophene-2-carboxylic acid {4-[2-fluoro-4-(2-oxo-2H-pyridin-1-yl)-phenylcarbamoyl]-2-methylamino-cyclopentylmethyl}-amide. Light yellow solid. 503.3 ([M+H]$^+$).

Example 34

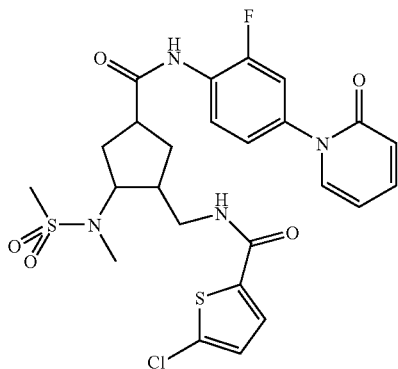

In analogy to example 26 5-chloro-thiophene-2-carboxylic acid {4-[2-fluoro-4-(2-oxo-2H-pyridin-1-yl)-phenylcarbamoyl]-2-methylamino-cyclopentylmethyl}-amide (example 33) was reacted with methane sulfonylchloride to give 5-chloro-thiophene-2-carboxylic acid [4-[2-fluoro-4-(2-oxo-2H-pyridin-1-yl)-phenylcarbamoyl]-2-(methanesulfonyl-methyl-amino)-cyclopentylmethyl]-amide. Light yellow solid. 581.2 ([M+H]$^+$).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

| Injection solutions can have the following composition: | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed is:

1. A compound of formula (I):

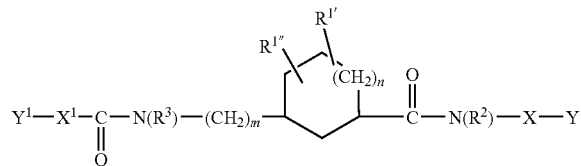

(I)

or a pharmaceutically acceptable salt thereof, wherein:
$R^{1'}$ is selected from the group consisting of: (1) cyano, (2) $C_{3-7}$ cycloalkyl-$C_{1-6}$ alkoxy, (3) hydroxy, (4) $C_{1-6}$ alkoxy, (5) halo $C_{1-6}$ alkoxy, (6) hydroxy-$C_{2-6}$ alkoxy-, (7) mono- or di-$C_{1-6}$ alkyl substituted amino, (8) ($C_{1-6}$ alkylsulfonyl)($C_{1-6}$ alkyl)amino-, and (9) heterocyclyl;
$R^{1''}$ is hydrogen; or
$R^{1'}$ and $R^{1'''}$ together with the same ring carbon atom to which they are attached, form a carbonyl group;
$R^2$ is hydrogen;
$R^3$ is hydrogen;
X is phenylene optionally substituted by one or more substituents independently selected from the group consisting of $C_{1-6}$ alkyl, halogen, and cyano;
$X^1$ is thienyl;
Y is pyridyl, morpholinyl, pyrazinyl, or pyrrolidinyl wherein one or two carbon atoms of said pyridyl, morpholinyl, pyrazinyl, or pyrrolidinyl is replaced with a carbonyl group;
$Y^1$ is hydrogen or halogen;
m is 0 or 1; and
n is 0.

2. A compound according to claim 1, wherein $R^{1'}$ is hydroxy.

3. A compound according to claim 1, wherein: $R^{1'}$ is selected from the group consisting of hydroxy, $C_{1-6}$ alkoxy and fluoro $C_{1-6}$ alkoxy; and $R^{1'''}$ is hydrogen.

4. A compound according to claim 3, wherein X is 1,4-phenylene optionally substituted by one substituent selected from the group consisting of halogen and $C_{1-6}$ alkyl.

5. A compound according to claim 4, wherein X is 2-fluoro-1,4-phenylene.

6. A compound according to claim 1 wherein Y is pyridyl, morpholinyl, or pyrazinyl, wherein one or two carbon atoms of said pyridyl, morpholinyl, or pyrazinyl is replaced with a carbonyl group.

7. A compound according to claim 6, wherein Y is pyridyl, pyrazinyl or morpholinyl, wherein one carbon atom of said pyridyl, pyrazinyl or morpholinyl is replaced with a carbonyl group.

8. A compound according to claim 7, wherein Y is 2-oxo-1-pyridyl, 2-oxo-1-pyrazinyl or 3-oxo-4-morpholinyl.

9. A compound according to claim 1 wherein $X^1$ is thienyl substituted by chloro.

10. A compound according to claim 9, wherein $Y^1$—$X^1$ forms 5-chloro-2-thienyl.

11. A compound according to claim 1, selected from the group consisting of:
    5-Chloro-thiophene-2-carboxylic acid {(1S,2S,4R)-4-[2-fluoro-4-(2-oxo-2H-pyridin-1-yl)-phenylcarbamoyl]-2-hydroxy-cyclopentyl}-amide,
    5-Chloro-thiophene-2-carboxylic acid {(1S,2S,4S)-4-[2-fluoro-4-(2-oxo-2H-pyridin-1-yl)-phenylcarbamoyl]-2-hydroxy-cyclopentyl}-amide,
    5-Chloro-thiophene-2-carboxylic acid {(1S,2S,4R)-2-hydroxy-4-[4-(3-oxo-morpholin-4-yl)-phenylcarbamoyl]-cyclopentyl}-amide,
    5-Chloro-thiophene-2-carboxylic acid {(1S,2S,4R)-4-[2-fluoro-4-(3-oxo-morpholin-4-yl)-phenylcarbamoyl]-2-hydroxy-cyclopentyl}-amide,
    5-Chloro-thiophene-2-carboxylic acid {(1S,2S,4R)-4-[2-fluoro-4-(2-oxo-2H-pyrazin-1-yl)-phenylcarbamoyl]-2-hydroxy-cyclopentyl}-amide,
    5-Chloro-thiophene-2-carboxylic acid {(1S,2S,4R)-2-hydroxy-4-[4-(2-oxo-2H-pyrazin-1-yl)-phenylcarbamoyl]-cyclopentyl}-amide,
    5-Chloro-thiophene-2-carboxylic acid {(1S,2S,4R)-2-hydroxy-4-[2-methyl-4-(2-oxo-2H-pyridin-1-yl)-phenylcarbamoyl]-cyclopentyl}-amide,
    5-Chloro-thiophene-2-carboxylic acid {(1S,2S,4R)-2-hydroxy-4-[4-(2-oxo-2H-pyridin-1-yl)-phenylcarbamoyl]-cyclopentyl}-amide,
    5-Chloro-thiophene-2-carboxylic acid {(1S,2S,4R)-4-[2-fluoro-4-(2-oxo-pyrrolidin-1-yl)-phenylcarbamoyl]-2-hydroxy-cyclopentyl}-amide,
    Thiophene-2-carboxylic acid {(1S,2S,4R)-4-[2-fluoro-4-(2-oxo-2H-pyridin-1-yl)-phenylcarbamoyl]-2-hydroxy-cyclopentyl}-amide,
    5-Chloro-thiophene-2-carboxylic acid {(1S,2S,4R)-4-[2-fluoro-4-(2-oxo-2H-pyridin-1-yl)-phenylcarbamoyl]-2-methoxy-cyclopentyl}-amide,
    5-Chloro-thiophene-2-carboxylic acid {(1S,2S,4S)-4-[2-fluoro-4-(2-oxo-2H-pyridin-1-yl)-phenylcarbamoyl]-2-methoxy-cyclopentyl}-amide,
    5-Chloro-thiophene-2-carboxylic acid {(1S,2S,4R)-2-(2,2-difluoro-ethoxy)-4-[2-fluoro-4-(2-oxo-2H-pyridin-1-yl)-phenylcarbamoyl]-cyclopentyl}-amide,
    5-Chloro-thiophene-2-carboxylic acid {(1S,2S,4S)-2-(2,2-difluoro-ethoxy)-4-[2-fluoro-4-(2-oxo-2H-pyridin-1-yl)-phenylcarbamoyl]-cyclopentyl}-amide,
    5-Chloro-thiophene-2-carboxylic acid {(1S,2S,4R)-2-ethoxy-4-[2-fluoro-4-(2-oxo-2H-pyridin-1-yl)-phenylcarbamoyl]-cyclopentyl}-amide,
    5-Chloro-thiophene-2-carboxylic acid {(1RS,2SR,4SR)-4-[2-fluoro-4-(2-oxo-2H-pyridin-1-yl)-phenylcarbamoyl]-2-hydroxy-cyclopentylmethyl}-amide,
    5-Chloro-thiophene-2-carboxylic acid {(1R,2S,4S)-4-[2-fluoro-4-(2-oxo-2H-pyridin-1-yl)-phenylcarbamoyl]-2-hydroxy-cyclopentylmethyl}-amide,
    5-Chloro-thiophene-2-carboxylic acid {(1R,2S,4S)-4-[2-fluoro-4-(2-oxo-2H-pyridin-1-yl)-phenylcarbamoyl]-2-hydroxy-cyclopentylmethyl}-amide, 5-Chloro-thiophene-2-carboxylic acid {(1S,2R,4R)-4-[2-fluoro-4-(2-oxo-2H-pyridin-1-yl)-phenylcarbamoyl]-2-hydroxy-cyclopentylmethyl}-amide, 5-Chloro-thiophene-2-carboxylic acid {(1RS,2SR,4SR)-2-hydroxy-4-[4-(3-oxo-morpholin-4-yl)-phenylcarbamoyl]-cyclopentylmethyl}-amide, 5-Chloro-thiophene-2-carboxylic acid {(1RS,2SR,4SR)-4-[2-fluoro-4-(2-oxo-2H-pyrazin-1-yl)-phenylcarbamoyl]-2-hydroxy-cyclopentylmethyl}-amide, and 5-Chloro-thiophene-2-carboxylic acid {(1RS,2SR,4SR)-4-[2-fluoro-4-(3-oxo-morpholin-4-yl)-phenylcarbamoyl]-2-hydroxy-cyclopentylmethyl}-amide.

12. A pharmaceutical composition comprising a compound according to claim 1 and a pharmaceutically acceptable excipient.

13. A pharmaceutical composition comprising a compound according to claim 11 and a pharmaceutically acceptable excipient.

14. A compound according to claim 2 wherein Y is pyridyl, morpholinyl, or pyrazinyl, wherein one or two carbon atoms of said pyridyl, morpholinyl, or pyrazinyl is replaced with a carbonyl group.

15. A compound according to claim 14, wherein Y is pyridyl, pyrazinyl or morpholinyl, wherein one carbon atom of said pyridyl, pyrazinyl or morpholinyl is replaced with a carbonyl group.

16. A compound according to claim 3 wherein Y is pyridyl, morpholinyl, or pyrazinyl, wherein one or two carbon atoms of said pyridyl, morpholinyl, or pyrazinyl is replaced with a carbonyl group.

17. A compound according to claim 16, wherein Y is pyridyl, pyrazinyl or morpholinyl, wherein one carbon atom of said pyridyl, pyrazinyl or morpholinyl is replaced with a carbonyl group.

18. A compound according to claim 2, wherein $Y^1$—$X^1$ forms 5-chloro-2-thienyl, Y is 2-oxo-1-pyridyl, and X is 2-fluoro-1,4-phenylene.

19. A compound according to claim 3, wherein $Y^1$—$X^1$ forms 5-chloro-2-thienyl, Y is 2-oxo-1-pyridyl, and X is 2-fluoro-1,4-phenylene.

20. A compound according to claim 4, wherein $Y^1$—$X^1$ forms 5-chloro-2-thienyl, Y is 2-oxo-1-pyridyl, and X is 2-fluoro-1,4-phenylene.

21. A compound according to claim 6, wherein $Y^1$—$X^1$ forms 5-chloro-2-thienyl, Y is 2-oxo-1-pyridyl, and X is 2-fluoro-1,4-phenylene.

* * * * *

UNITED STATES PATENT AND TRADEMARK OFFICE
CERTIFICATE OF CORRECTION

PATENT NO. : 7,678,917 B2 Page 1 of 1
APPLICATION NO. : 11/510831
DATED : March 16, 2010
INVENTOR(S) : Katrin Groebke Zbinden et al.

It is certified that error appears in the above-identified patent and that said Letters Patent is hereby corrected as shown below:

Claim 11, column 46, end of line 59, delete "{(1RS,2SR,4SR)-" and insert -- {(1SR,2RS,4SR)- --

Claim 11, column 46, end of line 62, delete "{(1R,2S,4S)-4-[2-"
and insert -- {(1RS,2SR,4SR)-4-[2- --

Signed and Sealed this

Eleventh Day of May, 2010

David J. Kappos
*Director of the United States Patent and Trademark Office*